(12) United States Patent
Yamamoto

(10) Patent No.: US 12,205,723 B2
(45) Date of Patent: Jan. 21, 2025

(54) PATHOLOGICAL DIAGNOSIS ASSISTING METHOD USING AI, AND ASSISTING DEVICE

(71) Applicant: JAPANESE FOUNDATION FOR CANCER RESEARCH, Tokyo (JP)

(72) Inventor: Noriko Yamamoto, Tokyo (JP)

(73) Assignee: JAPANESE FOUNDATION FOR CANCER RESEARCH, Tokyo (JP)

( * ) Notice: Subject to any disclaimer, the term of this patent is extended or adjusted under 35 U.S.C. 154(b) by 431 days.

(21) Appl. No.: 17/788,055

(22) PCT Filed: Dec. 25, 2020

(86) PCT No.: PCT/JP2020/048926
§ 371 (c)(1),
(2) Date: Aug. 9, 2022

(87) PCT Pub. No.: WO2021/132633
PCT Pub. Date: Jul. 1, 2021

(65) Prior Publication Data
US 2023/0045882 A1  Feb. 16, 2023

(30) Foreign Application Priority Data
Dec. 26, 2019  (JP) .................. 2019-236352

(51) Int. Cl.
*G16H 50/20* (2018.01)
*G06V 10/26* (2022.01)
(Continued)

(52) U.S. Cl.
CPC ........... *G16H 50/20* (2018.01); *G06V 10/267* (2022.01); *G06V 10/764* (2022.01);
(Continued)

(58) Field of Classification Search
CPC ........ G16H 50/20; G16H 10/40; G16H 30/40; G06V 10/7715; G06V 10/82;
(Continued)

(56) References Cited

U.S. PATENT DOCUMENTS 9,697,582 B2 *  7/2017  Grunkin ................. G06T 3/153
2010/0290692 A1  11/2010  Macaulay et al.
(Continued)

FOREIGN PATENT DOCUMENTS

JP  10-197522 A  7/1998
JP  2012-008027 A  1/2012
(Continued)

OTHER PUBLICATIONS

Cruz-Roa et al., "Automatic detection of invasive ductal carcinoma in whole slide images with Convolutional Neural Networks", Society of Photo-Optical Instrumentation Engineers, Mar. 20, 2014, vol. 9041, 904103;15 pages.
(Continued)

*Primary Examiner* — Allen H Nguyen
(74) *Attorney, Agent, or Firm* — Rankin, Hill & Clark LLP

(57) ABSTRACT

Diagnosis is assisted by acquiring microscopical observation image data while specifying the position, classifying the image data into histological types with the use of AI, and reconstructing the classification result in a whole lesion. There is provided a pathological diagnosis assisting method that can provide an assistance technology which performs a pathological diagnosis efficiently with satisfactory accuracy by HE staining which is usually used by pathologists. Furthermore, there are provided a pathological diagnosis assisting system, a pathological diagnosis assisting program, and a pre-trained model.

14 Claims, 17 Drawing Sheets

(51) Int. Cl.
| | |
|---|---|
| G06V 10/764 | (2022.01) |
| G06V 10/77 | (2022.01) |
| G06V 10/774 | (2022.01) |
| G06V 10/82 | (2022.01) |
| G06V 20/69 | (2022.01) |
| G16H 10/40 | (2018.01) |
| G16H 30/40 | (2018.01) |

(52) U.S. Cl.
CPC ........ *G06V 10/7715* (2022.01); *G06V 10/774* (2022.01); *G06V 10/82* (2022.01); *G06V 20/693* (2022.01); *G16H 10/40* (2018.01); *G16H 30/40* (2018.01)

(58) Field of Classification Search
CPC .. G06V 10/267; G06V 10/774; G06V 10/764; G06V 20/693
USPC .......................................................... 382/128
See application file for complete search history.

(56) References Cited

U.S. PATENT DOCUMENTS

| | | | |
|---|---|---|---|
| 2019/0087954 A1 | 3/2019 | Lloyd et al. | |
| 2019/0294108 A1* | 9/2019 | Ozcan | G06V 10/82 |
| 2020/0279126 A1* | 9/2020 | Nie | G06T 7/90 |
| 2022/0076411 A1* | 3/2022 | Georgescu | G06V 10/82 |
| 2022/0147760 A1* | 5/2022 | Dutta | G06F 18/24 |

FOREIGN PATENT DOCUMENTS

| | | |
|---|---|---|
| JP | 2012-073179 A | 4/2012 |
| WO | 2013/022688 A1 | 2/2013 |
| WO | 2019/191697 A1 | 10/2019 |

OTHER PUBLICATIONS

"Virtual slide technology", Optics, 2009, vol. 38, No. 11, pp. 586-587; English machine translation of relevant Information included; 3 pages.

"Official textbook for Deep Learning for General: JDLA Certificate Examination)" Oct. 22, 2018; English machine translation of relevant information included; 4 pages.

Coudray et al., "Classification and mutation prediction from non-small cell lung cancer histopathology images using deep learning", Nature Medicine, 2018, vol. 24, pp. 1559-1567; Supplementary Information pages included, 32 pages.

Kather et al., "Deep learning can predict microsatellite instability directly from histology in gastrointestinal cancer", Nature Medicine, 2019, vol. 25, pp. 1054-1056; 10 pages included.

English translation of Written Opinion of the International Searching Authority dated Mar. 23, 2021, Application No. PCT/JP2020/048926, 3 pages.

Japanese Gastric Cancer Association, "Japanese gastric cancer treatment guidelines 2018 (5th edition)", Feb. 14, 2020; discussed in the specification; English language included, 26 pages.

Ono et al., "ESD/EMR Guidelines for Gastric Cancer (Second Edition)", Feb. 2020, vol. 62, Gastroenterological Endoscopy, pp. 275-290; discussed in the specification, English translation of abstract included.

Schlegl et al., "Unsupervised Anomaly Detection with Generative Adversarial Networks to Guide Marker Discovery", Mar. 17, 2017, Austrian Federal Ministry of Science, Research and Economy, pp. 146-157; discussed in the specification.

The Cancer Genome Atlas Research Network, "Comprehensive molecular characterization of gastric adenocarcinoma", Nature, Sep. 11, 2014, vol. 513, pp. 202-209, Macmillan Publishers Limited; discussed In the specification.

Kather, et al., "Deep learning can predict microsatellite instability directly from histology in gastrointestinal cancer", Nature Medicine, Jul. 2019, vol. 25, pp. 1054-1056; discussed in the specification.

Ono, et al., "ESD/EMR Guidelines for Gastric Cancer", VII Pathology, Feb. 2014, vol. 56, No. 2, Gastroenterological Endoscopy, pp. 310-323; cited in the WO/ISA; English machine translation of abstract included.

Gatys, et al. "A Neural Algorithm of Artistic Style", Journal of Vision, Sep. 2016, vol. 16, 326. doi:https://doi.org/10.1167/16.12.326; English abstract only, 1 page.

Singapore Office Action, Letter accompanying Written Opinion and Written Opinion issued on Nov. 27, 2023, Application No. 11202251581P; 10 pages.

Extended European Search Report issue on Dec. 19, 2023, Application No. EP 20 90 5469; 8 pages.

Graham et al: "Classification of Lung Cancer Histology Images Using Patch-Level Summary Statistics", Progress in Biomedical Optics and Imaging, SPIE—International Society for Optical Engineering, Bellingham, WA, US, vol. 10581, Mar. 6, 2018 (Mar. 6, 2018), pp. 1058119-1058119, XP060104334; Cited in the Extended European Search Report.

* cited by examiner

Learning from Scratch

Fine tuning

Learning from Scratch

Fine tuning

Two-dimensional scatter diagram of morphological feature existing in certain tumor, by dimensionality reduction Localization of image patches from which points of scatter diagram are derived, in the whole view of lesion

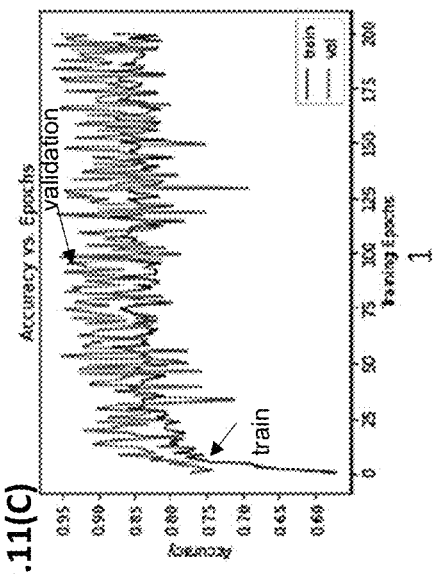
Fig.11(A)
Fig.11(B)
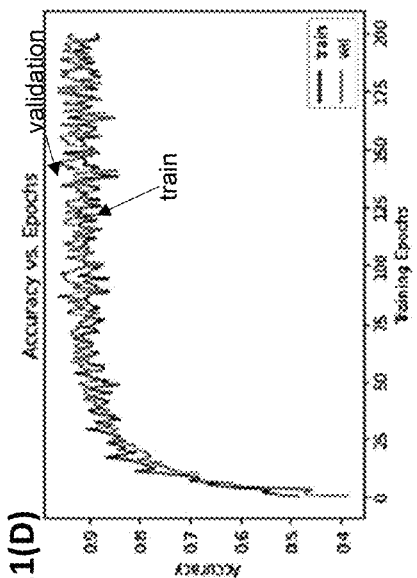
Fig.11(C)
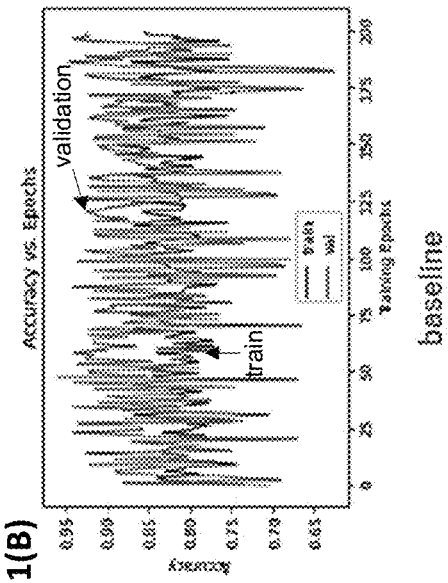
Fig.11(D)
2. Maximum value of accuracy rate in validation data 0.9683
Fig.11

Maximum value of accuracy rate in validation data for each model

Maximum value of accuracy rate in validation data for each model

Fig.15(A)
Preparation of image patches for determination
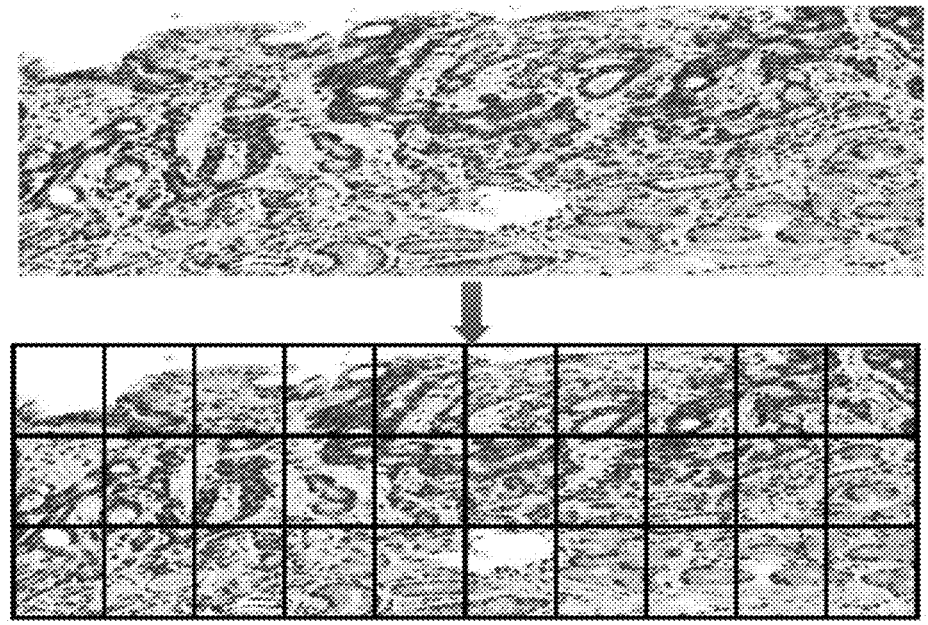
Fig.15(B)
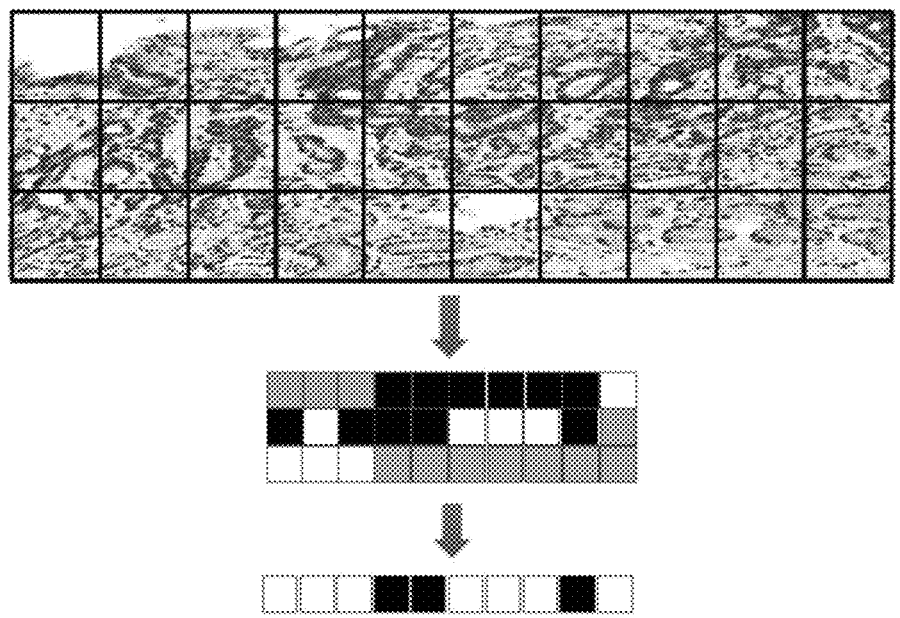
Fig.15

PATHOLOGICAL DIAGNOSIS ASSISTING METHOD USING AI, AND ASSISTING DEVICE

TECHNICAL FIELD

The present invention relates to a pathological diagnosis assisting method using AI, and an assisting device. The present invention also relates to a method of classifying a tumor from a pathological section of the tumor in order to determine a medical treatment strategy.

BACKGROUND ART

A pathological diagnosis which explores a tissue or a cell collected from a patient mainly with the use of an optical microscope and performs diagnosis plays a major role as a final diagnosis. Especially in a tumor, it is an important diagnosis for determining a treatment strategy, evaluating treatment efficacy, and determining prognosis.

For example, in the case of gastric cancer, when the gastric cancer is decided to be an early stage by the pathological diagnosis, endoscopic treatment such as EMR (endoscopic mucosal resection) or ESD (endoscopic submucosal dissection) is recommended. Data has been obtained that endoscopic treatment of early gastric cancer shows that QOL is better than surgical treatment, because of such advantages that burden on the patient is lighter, and recovery after the operation is better compared to the surgical operation. Because of this, it is recommended to perform the endoscopic treatment on a lesion that has high possibility of being completely cured by the endoscopic treatment.

Endoscopic resection is a recommended therapeutic method for early gastric cancer, but in principle, it is necessary for the adaptation to satisfy two points: (1) a risk of lymph node metastasis is extremely low, and (2) the tumor has such a size and is in such a position as to be capable of being collectively resected.

Guidelines (Non Patent Literatures 1 and 2) state that in a lesion in which the risk of the lymph node metastasis is estimated to be less than 1%, an equivalent result can be obtained by the endoscopic resection and the surgical resection, and in such a case, a benefit of selecting endoscopic treatment is significant. Furthermore, because it is known as evidence that the size of the intramucosal carcinoma, of which the risk of the lymph node metastasis is less than 1%, varies depending on a histological type of gastric cancer, particularly, on the degree of differentiation. Thus, a pathological diagnosis for deciding the histological type becomes important.

In Japan, the histological type of gastric cancer is roughly classified into two types of differentiated type cancer and undifferentiated type cancer, which are classification by the Japanese Gastric Cancer Association. This classification roughly corresponds to Intestinal (intestinal type) and Diffuse (diffuse type) of Lauren classification which is used internationally. The histological type of gastric cancer is described in WHO classification and the like, in addition to the classification by Japanese Gastric Cancer Association and Lauren classification, but the classification by Japanese Gastric Cancer Association is used herein unless otherwise specified. In differentiated type cancer, there is not a risk of lymph node metastasis until the size exceeds 3 cm, but in undifferentiated type cancer, there is a risk of lymph node metastasis when the size exceeds 2 cm (Non Patent Literatures 1 and 2). Based on these evidence, a guideline for endoscopic treatment of early gastric cancer is established.

However, in a cancer lesion, there is often heterogeneity in which a differentiated type and an undifferentiated type are mixed within the same lesion, which gives a great influence on the selection of the treatment strategy.

Because of this, before performing the endoscopic resection, firstly, a biopsy specimen is obtained, thereby information on the histological type and the degree of differentiation of cancer is obtained; and also a preoperative diagnosis is performed which determines the size of cancer from endoscopic views. By the preoperative diagnosis, it is decided whether or not the endoscopic treatment can be adapted, and a resection range in the case of the adaptation is determined; and when it is decided that the endoscopic treatment can be adapted, the operation is performed. However, it is difficult to accurately measure the size and invasion depth by the endoscopic view before the operation; and accordingly, an endoscopically resected specimen is histopathologically explored, and the curability of the medical treatment results in being decided.

If it is decided that the endoscopic resection is not curable, by the histological findings of the endoscopically resected specimen, the patient becomes an object of additional surgical resection. Specifically, in a case where the histological type of the resected specimen has included undifferentiated type cancer having a size of exceeding 2 cm, in a form of mixing in a lesion in which differentiated type cancer is predominant, the case is decided as non-curatively resected; and additional surgical resection and lymph nodes dissection are adapted. In addition, even in the case of a lesion in which the differentiated type is predominant, a lesion in which there is an undifferentiated type lesion in a submucosal layer (SM) infiltration portion is decided as the non-curative resection, and the additional surgical resection is adapted thereto.

In order to decide such curability, the pathologist decides the distribution and invasion depth of the respective components of the differentiated type and undifferentiated type in the whole lesion, reconstructs the whole view of the lesion, and makes a comprehensive decision. Specifically, the pathologist makes the comprehensive decision according to the following procedure, and performs the diagnosis (FIG. 17).

(1) Preparation of Tissue Specimen

An endoscopically resected specimen is fixed with formalin, and then the pathologist cuts out the tissue specimen. The resected tissue pieces are cut out in parallel at intervals of 2 to 3 mm, and a macroscopic photograph of the fixed specimen containing the cutting out section line is taken.

A paraffin block is prepared through specimen treatment (dehydration, clearing and paraffin immersion of tissue), and a specimen slide is prepared by slicing, staining and sealing. In the prepared specimen slide, the cut-out tissue sections are arranged in parallel (see FIG. 17, specimen slide).

(2) Microscopical Observation of Tissue Specimen, and Diagnosis

Microscopical observation is performed, and the histological type is recorded. In a case where two or more histological types coexist, all the histological types are described in the order of superiority, for example, such as tub1 (tubular adenocarcinoma, well differentiated type)>por (poorly differentiated adenocarcinoma). All sections of the pathological tissue specimen are microscopically examined, and the degree of differentiation (differentiated type or undifferentiated type) of the cancer is determined.

The results of the microscopical observation are drawn on the section lines in a macroscopic photograph having the section lines drawn, in such a form that a range in which the differentiated type is distributed is colored with a red line and the undifferentiated type is colored with a blue line (see FIG. 17, Integration).

The degree of differentiation is written for each section, and thereby, the whole view of the lesion is reconstructed. By use of the reconstructed diagram, it is comprehensively decided whether or not the distribution and size of undifferentiated components exceed 2 cm, whether or not an undifferentiated type exists in a submucosal layer (SM) infiltration portion, and the like.

In other words, a specimen slide is prepared from a paraffin section, then the histological type is determined under a microscope and is classified (Classification), the result is reconstructed into a whole view of the lesion (Integration), and comprehensive decision is made from the whole specimen (Decision). Comprehensive decision is made through the above three steps.

A certain amount of time and experience are required, in order to make the comprehensive decision and diagnosis from the microscopic examination of a prepared slide. For example, in a case of endoscopically resected early gastric cancer, even a skilled pathologist usually needs about 30 minutes for the steps from the Classification to the Decision. In addition, it is said that an experience for about 12 to 13 years is required in order to become a skilled pathologist with a certain amount of experiences. Because of this, there is a need for a method or a system that can improve an efficiency of diagnosis by skilled pathologists and shorten the time to decision, or that can assist inexperienced pathologists so as to perform accurate diagnosis.

In recent years, attempts have been started that intend to use the AI (artificial intelligence) for assistance of image diagnosis, which has dramatically improved an accuracy of image recognition by machine learning, and an assisting device for assisting a detection of a lesion site is being practically used in endoscopic imaging, fundus examination, and the like.

Also in the diagnosis assistance of pathological tissues, there are discloses devices (Patent Literatures 1 to 3), which assist diagnosis with the use of a computer system. These devices are mainly devices and methods for detecting a region pathognomonic for a lesion from a local tissue image, and for assisting a pathological diagnosis.

CITATION LIST

Patent Literature

[Patent Literature 1]
  Japanese Patent Application Laid-Open No. H10-197522
[Patent Literature 2]
  Japanese Patent Application Laid-Open No 2012-8027
[Patent Literature 3]
  Japanese Patent Application Laid-Open No 2012-73179

Non Patent Literature

[Non Patent Literature 1]
  Guideline for gastric cancer treatment, for medical doctors, fifth revised edition, January 2018, edited by Japanese Gastric Cancer Association, Kanehara & Co., Ltd.
[Non Patent Literature 2]
  Hiroyuki Ono et al., ESD/EMR guideline for gastric cancer (Second edition), February 2020, Gastroenterological endoscopy, Vol. 62, pp. 275 to 290
[Non Patent Literature 3]
  Schlegl, T. et al., IPMI2017: Information Processing in Medical Imaging, pp. 146 to 157
[Non Patent Literature 4]
  The Cancer Genome Atlas Research Network, 2014, Nature, Vol. 513, pp. 203 to 209
[Non Patent Literature 5]
  Kather, J. N., et al., 2019, Nature Medicine, Vol. 25, pp. 1054 to 1056.
[Non Patent Literature 6]
  Gatys, L. A. et al., Journal of Vision September 2016, Vol. 16, 326. doi: https://doi.org/10.1167/16.12.

SUMMARY OF INVENTION

Technical Problem

However, any of these literatures only searches sites pathognomonic for lesions, and detects the presence or absence of the lesions. In other words, whether the lesion is "cancer (malignant tumor)" or "non-cancer (non-malignant tumor)" is determined. In other words, any of these literatures maps the result of determination of cancer or non-cancer by AI. Different from this, the present invention visualizes heterogeneity within cancer by mapping the decision results in which cancer is further classified on the basis of clinical evidence with the use of AI. In other words, the present invention constructs a system which not only decides cancer or non-cancer, but also includes all processes including continuously performing detailed classification in a lesion such as tubular adenocarcinoma or poorly differentiated adenocarcinoma (Classification), reconstructing the whole lesion (Integration), and comprehensively decides the lesion (Decision). As described above, in order to decide whether there is a high possibility of complete cure by the endoscopic treatment, or additional surgical resection is necessary, it is necessary not only to simply determine whether a lesion is cancer or not at a lesion site, but also to recognize fine classification in the lesion and its distribution and proportion while considering the degree of continuous and uneven differentiation in the lesion, and to comprehensively evaluate the lesion.

An object of the present invention is to provide a system and a method for visualizing a change in the degree of differentiation in a tumor and the heterogeneity of the tumor, and assisting diagnosis, by precisely analyzing the inside of a lesion while recording the position in the lesion, forming a map in a lesion region, and reconstituting the whole lesion. According to the system and method of the present invention, it is possible to provide a system and method for efficiently performing diagnosis by visualizing the heterogeneity in the lesion without depending on the skill of a pathologist.

Solution to Problem

The present invention relates to the following pathological diagnosis assisting method, system, program, and pretrained model.

(1) A pathological diagnosis assisting method including: an image acquisition step of continuously acquiring microscopical observation image data of a tissue specimen; a step of dividing the image data into a predetermined size while maintaining positional information and obtaining an image patch; a decision step of determining a histological type for each image patch, on the basis of training data obtained by machine learning; and a reconstructing step of displaying the determined histological type at each position.

(2) The pathological diagnosis assisting method according to (1), wherein the reconstructing step of displaying the histological type determined by machine learning at each position displays a change in the degree of differentiation in the tumor and heterogeneity of the tumor.

(3) The pathological diagnosis assisting method according to (1) or (2), wherein the machine learning is based on a neural network.

(4) The pathological diagnosis assisting method according to (3), wherein the neural network uses images having resolutions of 0.1 µm/pixel to 4 µm/pixel, as images for training.

(5) The pathological diagnosis assisting method according to any one of (1) to (4), wherein the tissue specimen is derived from a cancer tissue and pathological diagnosis of cancer is assisted.

(6) The pathological diagnosis assisting method according to any one of (1) to (5), wherein the tissue specimen is an HE-stained specimen or an immunohistochemically stained specimen.

(7) The pathological diagnosis assisting method according to (6), wherein when the HE-stained specimen is a non-standardized specimen, a neural style transfer method is used, a quasi-immunohistochemically stained specimen is prepared, and the histological type is determined by a learning model which has learned an immunohistochemically stained specimen image.

(8) A pathological diagnosis assisting system including: image acquisition means for continuously acquiring microscopical observation image data of a tissue specimen; image processing means for dividing the image data into image patches having predetermined sizes while maintaining positional information; classification means for determining a histological type for each divided image on the basis of training data obtained by machine learning; and reconstructing means for displaying the classified histological type at each position.

(9) The pathological diagnosis assisting system according to (8), wherein the image processing means includes means for standardizing a tissue stained specimen.

(10) The pathological diagnosis assisting system according to (8) or (9), wherein the machine learning is a neural network.

(11) The pathological diagnosis assisting system according to (10), wherein the neural network uses a parameter value of a histological type, which has been obtained in advance by transfer learning.

(12) The pathological diagnosis assisting system according to any one of (8) to (11), wherein a disease assisted by the pathological diagnosis assisting system is cancer.

(13) A pathological diagnosis assisting program causing a computer to execute processes of: dividing acquired image data into a predetermined size while maintaining positional information; using a learning model learned by use of training data; determining a histological type for each divided image by machine learning; and displaying the determined histological type at each position to reconstitute the whole lesion.

(14) The pathological diagnosis assisting program according to (13), including a process of continuously acquiring microscopical observation images of a tissue specimen.

(15) A pre-trained model for determining a histological type of image data on the basis of microscopical observation image data of a tissue specimen, including: an input layer for which microscopical observation image data of a tissue specimen of interest is divided into a predetermined size, and to which the divided data is input; an output layer for displaying a histological type decision result of the divided image data at each position of the tissue specimen, the pre-trained model being for causing a computer to function, wherein the computer includes a classifier for classifying a histological type based on data learned on the basis of the histological type image of which has been decided by a doctor, as training data, and determines a histological type of microscopical observation image data that has been input and divided into a predetermined size, and displays the histological type at each position of a tissue specimen.

(16) The pre-trained model according to (15), wherein the training data is obtained by preprocessing images.

(17) A method for diagnosing a patient by use of a pathological diagnosis assisting method according to any one of (1) to (7), on the basis of a reconstructed diagram in which an analysis result is expressed.

(18) A method for treating a patient including: using the pathological diagnosis assisting system according to any one of (8) to (12); and determining a treatment strategy based on the obtained reconstructed diagram.

BRIEF DESCRIPTION OF DRAWINGS

FIG. 11 illustrates diagrams illustrating a construction of a two-class classifier for gastric cancer with the use of an HE-stained specimen, and the results, in which FIG. 11(A) illustrates an example of image data for learning; FIGS. 11(B) to 11(D) illustrate examples of learning curves; FIG. 11(B) illustrates an investigation of a baseline; and FIGS. 11(C) and 11(D) illustrate adjustment results.

FIG. 12 illustrates diagrams illustrating the construction of a three-class classifier of gastric cancer with the use of an HE-stained specimen, and the results, in which FIG. 12(A) illustrates an example of image data for learning; and FIGS. 12(B) to 12(G) illustrate results of using 12(B) Resenet 18, 12(C) Inception v3, 12(D) Vgg-11 with batch normalization (Vgg-11_BN), 12(E) Densenet121, 12(F) Squeezenet 1 (Squeezenet version 1.0), and 12(G) Alexnet, respectively.

FIG. 13 illustrates diagrams illustrating the construction of a three-class classifier of thyroid cancer with the use of an HE-stained specimen, and the results, in which FIG. 13(A) illustrates an example of image data for learning; and FIGS. 13(B) to 13(G) illustrate results of using 13(B) Densenet 121, 13(C) Resenet 18, 13(D) Squeezenet 1, 13(E) Inception v3, and 13(F) Vgg-11_BN, respectively.

FIG. 15 illustrates diagrams illustrating a method of classifying a histological type in consideration of a thickness of a mucous membrane, in which FIG. 15(A) illustrates an example in which three image patches have been obtained in the vertical direction according to the thickness of the mucous membrane; and FIG. 15(B) illustrates a procedure for creating a map based on the classification results of the image patches.

DESCRIPTION OF EMBODIMENTS

Figure 1:
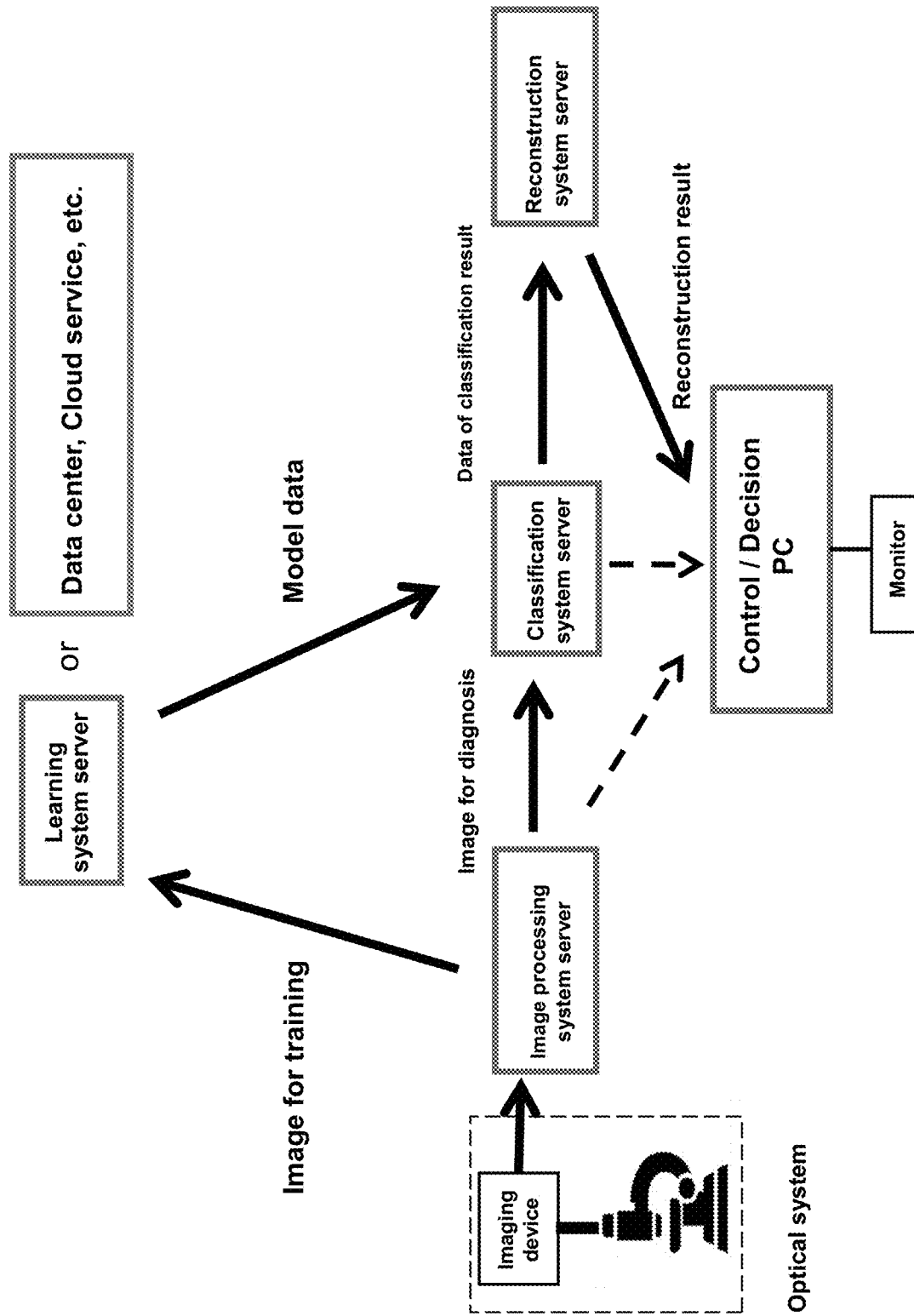
FIG. 1 shows one embodiment of a pathological diagnosis assisting system.
Figure 2:
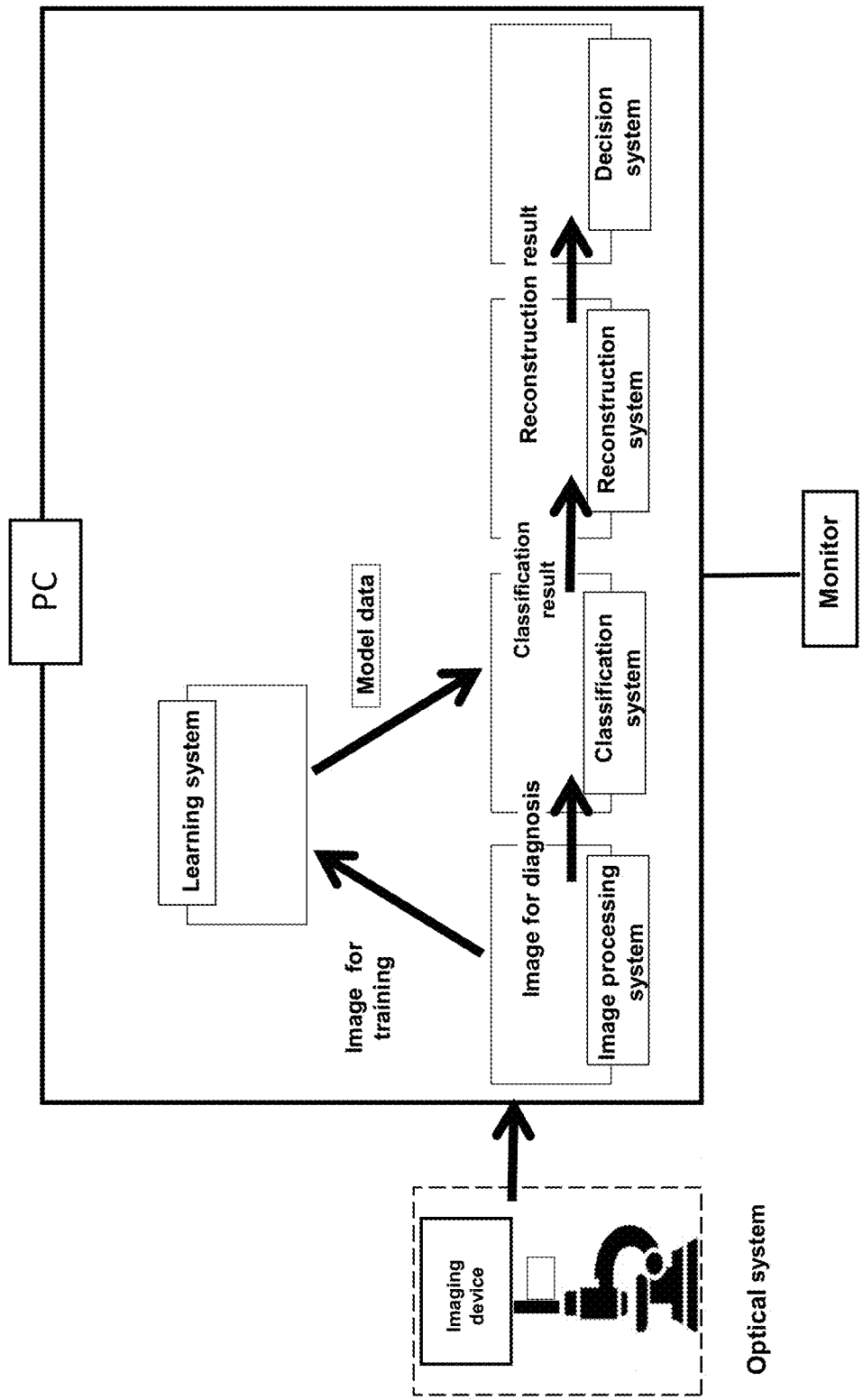
FIG. 2 shows another embodiment of a pathological diagnosis assisting system.

Firstly, an embodiment of a pathological diagnosis assisting system according to the present invention will be described (FIGS. 1 and 2). Devices necessary for assisting the pathological diagnosis are systems of an optical system, an image processing system, a learning system, a classification system, a reconstruction system, and a control/decision system. Specifically, the devices are a microscope, an imaging device connected to the microscope, a device that performs image processing, and a learning device that learns images after the image processing and determines a parameter, and a computer system that determines classification based on the parameter which the learning device has determined with the use of the image for diagnosis after the image processing, and reconstructing the image of which the classification has been determined. The computer systems of the image processing system, the classification system, the learning system, the reconstruction system, and the control/decision system can be each constructed in a server as a system, as is illustrated in FIG. 1. Here, an example is shown in which the systems are constructed on different servers, respectively, but the system may be constructed as a system that is controlled by different programs on one server.

In addition, when a PC is used which is provided with a high-performance CPU or GPU as illustrated in FIG. 2, the functions of the image processing, the learning, the classification, the reconstruction, and the decision can be sufficiently performed in sequence in one PC. Alternatively, although not shown here, the image processing system, the learning system, the classification system, the reconstruction system and the control/decision system may be constructed so that the systems are performed by different PCs, respectively. In addition, it is needless to say that the present invention is not limited to the construction, and it is possible to construct a system suitable for a situation of each facility. Embodiments will be shown and described below.

Embodiment 1

A system will be described which uses a server. Computer systems other than the control/decision PC are installed and constructed on the respective servers (FIG. 1). An optical system includes a bright-field optical microscope and an imaging device, and an operator sets an imaging field under the optical microscope, and acquires a pathological tissue image with the imaging device. The consecutive images may be acquired by manual movement of the field of view, or by use of a motorized stage. In addition, an image may be acquired from a WSI (Whole Slide Image) of a tissue specimen, in other words, a so-called virtual slide. An image acquired by the imaging device is transmitted to a server of the image processing system, and is subjected to image processing.

In the server of the image processing system, processings are performed which include general image processing method such as channel separation of RGB, histogram analysis of images and binarization of the image, and processing of identifying and extracting epithelial tissues from an HE-stained image which will be described later, and then the image is divided into appropriate sizes to create image patches (For information, the image patches are also referred to as image tiles or image grids). After that, in the case of an image for training, a label is attached such as non-tumor (normal), differentiation or undifferentiated, and is transmitted to the learning system server; and in the case of an image for diagnosis, the label is not attached, and the image is transmitted to the classification system server As the learning system server, not only a local server in the own facility but also a cloud service or a data center can be used. In the learning system, parameters to be used in the classification system are determined, and are sent to the classification system server.

In an embodiment which uses the cloud service or the data center as shown in FIG. 1, it becomes possible to perform learning with the use of a large-scale image data set, while utilizing high-performance GPU resources. For example, by uploading annotations concerning which region has been decided as a disease region, together with images, from many facilities, pathologists in many facilities can participate in the creation of classification criteria, and can attempt to uniformize diagnosis criteria. In addition, in order to create a high-quality decision system, it is possible to manage the accuracy of classification criteria, by limiting participation in uploading images and annotations, according to the degree of experience and expertise of the pathologists.

The classification system server has a function of performing classification decision using parameters which have been determined by the learning system, for the image for diagnosis, which the classification system server has received from the image processing system, and sending result data to the reconstruction system.

As for the diagnosis image, a plurality of image patches in the vertical direction, which are usually three to five image patches, are obtained according to the thickness of the mucous membrane. In addition to this order in the vertical direction, numbers are assigned to the image patches, which retain an order in the horizontal direction of the tissue specimen sections, and indicate positions in the whole specimen. Accordingly, results (being output in 0, 1 and 2) are stored for each slice, which indicate to which class of the differentiated type, the undifferentiated type, and non-tumor (normal) the image has been determined by analysis, and are sent to the reconstruction system.

In the reconstruction system, a one-dimensional vector is obtained for each slice, by determining that the part is undifferentiated in which even one of three image patches in the vertical direction has been determined to be undifferentiated, for each vertical line, is converted to a gray scale, and is drawn as an image in which the differentiated type corresponds to black and the undifferentiated type corresponds to white; and a straight line is obtained in which the differentiated type and the undifferentiated type are indicated by white and black. The straight lines are arranged on the basis of the coordinates of the start point of each slice and the coordinates of the start point of the cancer portion, and a reconstruction diagram of the analysis result is obtained.

Embodiment 2

The system will be described below which performs calculations of an image processing system, a classification system, a reconstruction system, a decision system and a learning system, in a PC (FIG. 2). The optical system is the same as that in the first embodiment, but all the systems for performing calculations of the image processing system, the classification system, the reconstruction system, the decision system, and the learning system are configured to be constructed in a single PC. The calculations are performed in a single PC, but the basic processings which are performed therein are the same as those in the first embodiment.

In deep learning using a neural network, GPGPU (General-purpose computing on graphics processing units) which is a technology that uses a GPU as a computing unit has dramatically shortened the time and improved the performance, in the processing of the calculation which is repeatedly performed for a data tensor. In any case of a server in the own local facility or the system which uses the PC shown in FIG. 2, it becomes possible to perform learning with a large amount of image data in the own facility, by introducing a high-performance GPU.

EXAMPLES

Firstly, gastric cancer will be described as an example, but it is needless to say that the pathological diagnosis assisting method according to the present invention can be applied to any diseases as long as the disease requires a pathological diagnosis, by causing the assisting devices to learn appropriate images with the use of an appropriate classifier. In addition, as will be described later, the pathological diagnosis assisting method according to the present invention can obtain a high accuracy rate by selecting an appropriate model according to an organ. Here, the pathological diagnosis assisting method performs the analysis with the use of a neural network having a high image recognition capability, in particular, a convolutional neural network; but new models for image recognition such as EfficinentNet, Big Transfer (BiT) and ResNeSt can also be used. In addition, Vision Transformer (ViT), i.e., models used in field of natural language processing such as Transformer, Self-Attention or BERT (Bidirectional Encoder Representations from transformers) applied to an image processing could be used. Furthermore, it is needless to say that a model with high image recognition capability can be used which will be developed in the future.

[Pathological Diagnosis Assisting Method]

Figure 3:
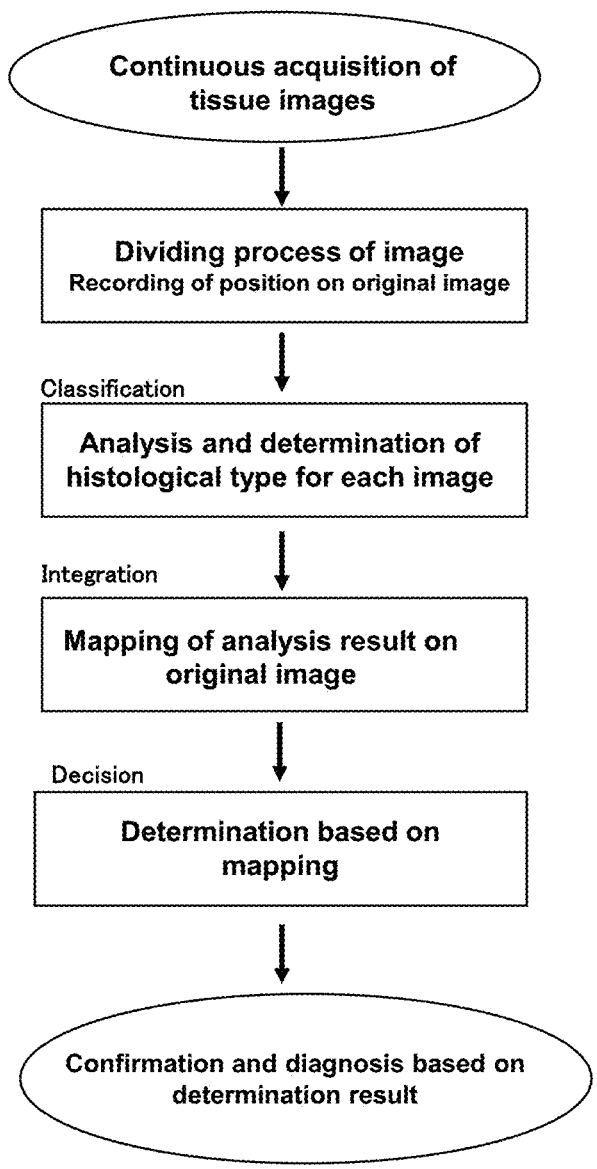
FIG. 3 shows a flow diagram of an embodiment of a pathological diagnosis assisting method.

The pathological diagnosis assisting method will be described with reference to an example of a gastric cancer tissue specimen which has been endoscopically resected (FIG. 3). Tissue images are continuously acquired by an optical system device, as in the conventional case. At this time, positional information is acquired as the coordinates on the specimen and is transmitted to the reconstruction system server. The acquired image is subjected to image processing in an image processing system, and then is subjected to division processing to be divided into appropriate sizes; and thereby image patches are created. The method of creating the image patches and training the learning system can greatly reduce the time and effort necessary for annotation, and accordingly, it is very useful for improving the efficiency of the development cycle including selection and adjustment of a model.

Figure 4:
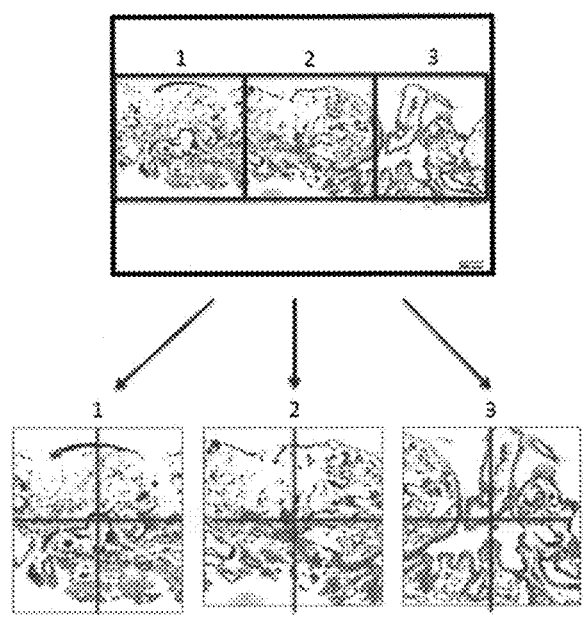
FIG. 4 shows a diagram showing an example of a method for creating an image patch.

The image patch here refers to image data which covers all morphology existing in a tumor. The example shown in FIG. 4 shows an example of cutting out upper and lower margins from a original image, obtaining only the tissue portion, dividing the tissue portion into three parts from the left, obtaining three sheets of small images 1 to 3, further dividing each of the small images into two in vertical and horizontal directions to obtain four sheets, and thereby creating image patches of 3×4=12 sheets. As for the small image 1 among the three divided images, four small patches result in being obtained by dividing the small image into two in the vertical and horizontal directions. If the small image 1 has 512×512 pixels, four image patches having 256×256 pixels result in being obtained. In order to obtain a high accuracy rate, it is very important to unify the tissue components included in each piece of training data. The method of using the image patch is very effective for obtaining a high-performance model, because a histological image in one image patch can become single, and accordingly high-quality training data can be obtained.

The positional information on the original image is already sent to the reconstruction system. In the classification system, analysis and decision are performed for each image patch based on parameters which have been created on the basis of the image for learning. The decision result is sent to the reconstruction system and is mapped on the original image. The decision system decides the presence or absence of the necessity of additional surgical resection based on the results of the reconstruction system, and displays the result on a monitor. The doctor corrects the reconstructed diagram by AI on the basis of his/her own microscopical observation result, confirms the decision, and performs diagnosis (FIG. 3).

[Construction of Classification/Decision System for Histological Type]

1. Development Environment

As for a development environment, Python was used as a programming language, and development was performed by Pytorch as a deep learning framework and Keras using TensorFlow as a back-end.

2. Data for Learning

In order to construct a diagnosis assisting system using AI, it is necessary to cause the system to learn image data beforehand so that when image data of a tissue specimen has been newly input, the system can accurately classify the histological type. For this purpose, it is necessary to prepare data for learning, in which each histological type is decided by a skilled pathologist. The data for learning includes images for learning and labels such as non-tumor (normal), tumor, and histological type of the tumor, which the pathologist has determined; and is used as supervised learning.

Images for learning were created with the use of pathological tissue images of differentiated type gastric cancer and undifferentiated type gastric cancer. In the tissue of gastric cancer, non-cancer cells are mixed together with cancer cells, and most of the cells are inflammatory cells such as lymphocytes and macrophages, and non-epithelial cells such as fibroblasts. The classification system for the differentiated type and the undifferentiated type, which is prepared herein, is based on the morphology and structure of cancer, and accordingly non-epithelial cells are not necessary. Then, firstly, a tissue specimen is used that has been subjected to immunohistochemistry (IHC) staining based on cytokeratin which is an intracellular protein possessed by epithelial cells, instead of a specimen stained with hematoxylin/eosin (HE) which is used for general daily diagnosis.

Cytokeratins are classified into 20 subtypes, exist in all epithelia, and stable expression is observed even after tumor formation. For example, the cytokeratin is expressed in cancers of the esophagus, stomach, colon, liver, bile duct, mammary gland, prostate and the like. A tissue specimen in which only the epithelial cell is colored is obtained by using an antibody against cytokeratin which is expressed on an epithelial cell to bind to the cytokeratin on the tissue section, and coloring the cytokeratin. By acquiring an image from the colored tissue specimen, it becomes possible to discriminate morphological classification only for the epithelial tissue.

The immunohistochemistry staining based on cytokeratin can stain only epithelial tissues, and accordingly, it is effective as image data at the time when the morphological classification is discriminated with the use of only the structure of the epithelial tissue. Accordingly, as long as cancer is derived from an epithelial tissue, the pathological diagnosis assisting method using the immunohistochemistry staining based on cytokeratin can be applied to most of cancers. Cancers derived from epithelial tissues to which immunohistochemistry staining based on cytokeratin can be suitably applied include gastric cancer, colon cancer, pancreatic cancer, bole duct cancer, breast cancer and lung cancer; and the cancer for which the staining is particularly effective is adenocarcinoma. In other words, the classification method with the use of the immunohistochemistry staining based on cytokeratin can be applied to many cancers.

On the other hand, a pathological diagnosis in actual clinical practice is mainly performed with the use of an HE-stained specimen. When a pathologist observes a tissue specimen by using an optical microscope, the pathologist unconsciously identifies and extracts epithelial tissue and non-epithelial tissue from a tissue image of the HE-stained specimen, visually recognizes the tissues, morphologically decides for only the epithelial tissue, and diagnoses cancer. This step which the pathologist unconsciously performs can be converted to and generate an image equivalent to that by immunohistochemistry staining based on cytokeratin, if the HE-stained specimen is subjected to conversion by an image processing with the use of AI, or to image conversion or image generation with the use of deep learning. It is possible to cause the AI to learn and analyze images, by performing image conversion or image generation on the basis of the same HE specimen as that used in the actual clinical practice. By using the HE-stained specimen, it becomes possible to apply the pathological diagnosis assisting method to tumors regardless of the type. In addition, as will be described later, in a case where the HE-stained image cannot be used as it is, for example, in cases where there is a difference in the specimen color between specimens in which fading has progressed, specimens in which staining is light, or specimens from different facilities, the pathological diagnosis assisting system can make a determination if the HE-stained image is processed into a pseudo-cytokeratin-stained image with the use of a neural style transfer method.

An image suitable for morphological classification of the epithelial tissue can be obtained also by combining general image processing techniques such as RGB channel separation, image histogram analysis, and image binarization, to each other. In addition, an image for learning suitable for the morphological classification can be generated by image generation which uses a technique of deep learning such as GAN (Generative Adversarial Network). When the deep learning is used, by training a pair of an HE-stained specimen and a continuous immunohistochemically stained specimen based on cytokeratin, it becomes possible to obtain a converted image corresponding to the image by pixel. Such preprocessing of images is most important for efficiency and speed-up of learning, and also leads to correcting and standardizing differences in color of images due to difference in stained state between facilities, difference in thickness between specimens, and the like, and also leads to standardization of training images and diagnosis images.

Figure 5:
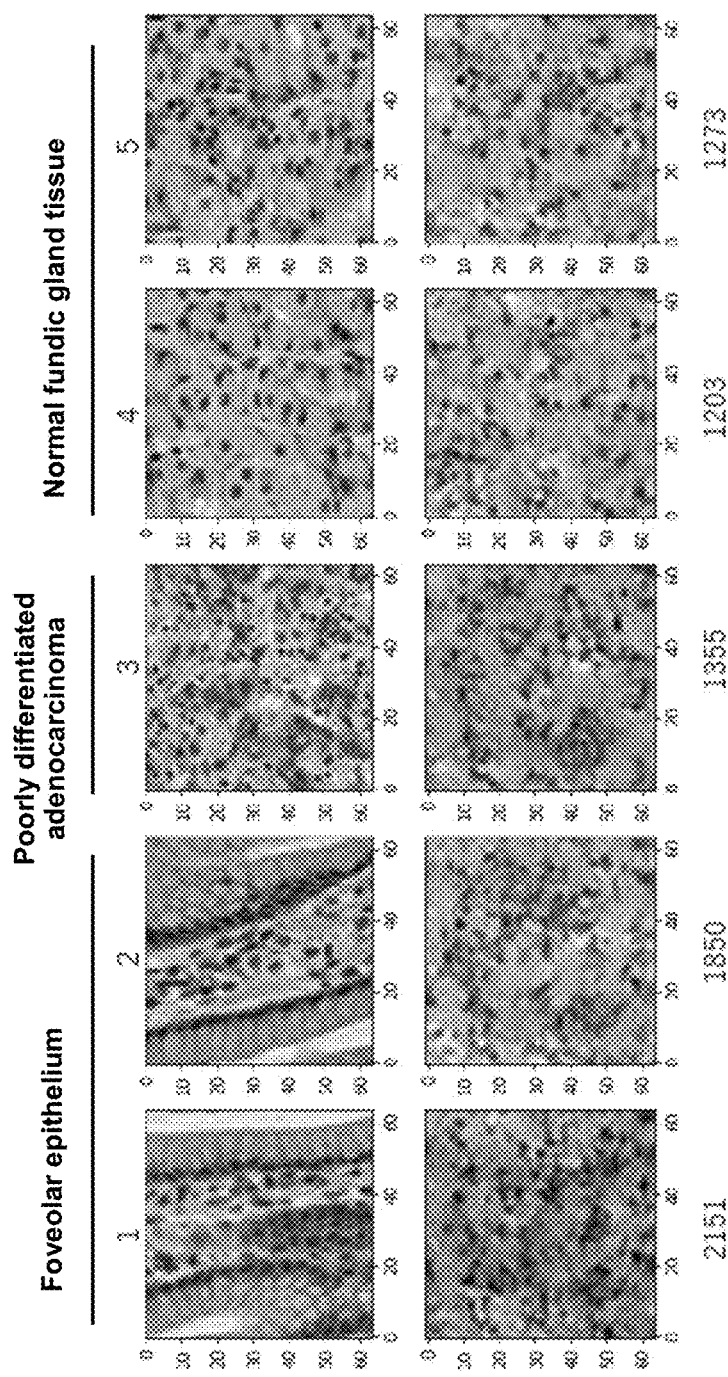
FIG. 5 shows a diagram showing an example of a decision system by anomaly detection based on DCGAN of normal tissues.

By using image generation by GAN, it becomes also possible to determine less frequent lesions. In a case of a lesion having a low frequency, it is difficult to prepare a large amount of images for learning, and accordingly, it is difficult to make a determination with conventional classification models. However, a method in which GAN and machine learning are combined for detecting abnormality (AnoGAN or the like) can quantify and determine the degree of the abnormality in an image with the use of a GAN model which have already trained normal tissues. In FIG. 5, determination is performed with the AnoGAN model which detects abnormality by using the GAN model (DCGAN: Deep Convolutional GAN) which has trained only normal fundic gland tissue images with a convolutional neural network model (Non Patent Literature 3). As a result of digitizing the degree of abnormality, a numerical value of 1200 range is obtained for the trained normal fundic gland tissues (4 and 5), but a large numerical value is obtained for the images of foveolar epithelium (1 and 2) and poorly differentiated adenocarcinoma (3) which have not been trained. By using an abnormality detection method in which machine learning is performed with the use of images of normal tissues, it becomes possible to detect the abnormality as a difference from the normal tissue, even in a case of a lesion for which it is difficult to prepare a large amount of images for learning.

For information, no matter which staining method is used, it is important to prepare the pathological specimen to be used with the use of a device/reagent and a procedure of which the qualities are controlled so that the color tone and shade of staining can also be determined, in addition to the preparation of a uniform section.

Because the performance of the classification system is determined by two factors of the performance of the neural network model and the training image, the training image plays an important role in the construction of the classification system. In a case of transfer learning, an excellent model can be used that has been devised in a competition which uses large-scale image data, but the image to be trained must be prepared by the user in light of his/her own problem. It is necessary for the user to devise an image for learning suitable for a task to be realized in each field. In the following example of the endoscopic resection specimen of gastric cancer, an image patch was created based on images obtained from a normal portion and a cancer portion of a mucous membrane so that the normal mucosal portion, the differentiated type cancer, and the undifferentiated type cancer can be generally distinguished.

The resolution of the image can be preferably employed from the resolutions of microscopes which are commonly used in a range of about 0.1 µm/pixel to 4 µm/pixel depending on the combination of an objective lens and an imaging lens, preferably in a range of 0.2 µm/pixel to 4 µm/pixel, and more preferably in a range of 0.25 µm/pixel to 2 µm/pixel. As a size of the image, a range from approximately 34×34 pixels to 1024×1024 pixels was used. If it is desired to identify a morphology localized to a very small area, training can be performed with the use of a small image with high resolution. In addition, in Example using the cytokeratin immunohistochemistry specimen, training was performed based on images having the size of the 256×256 pixels, but depending on a model to be used for training, it becomes also necessary to use larger images. The size of the image can be appropriately selected according to the problem to be achieved, the state of the tissue, and the training model.

Here, the image patches which are used for training and diagnosis are made as small as possible in such a range as to be visually recognized. By reducing the size of the image patch, it becomes possible to make the morphology of the tissue included in one image patch close to single. Furthermore, when a small image patch including only a single morphology is used, it becomes possible to analyze a tumor having a marginal morphology from a new viewpoint, which has been difficult to be determined by a conventional two division method based on differentiation/undifferentiation. In the image patches which are created for images for diagnosis, images are obtained that cover all pathological tissue morphologies contained in an individual tumor, together with positional data within the tumor tissue.

3. Deep Learning

A data set for training was prepared by acquiring a tissue image of a cancer portion from the specimen that was subjected to immunohistochemistry staining which used an anti-cytokeratin antibody, subjecting the tissue image to augmentation processing such as rotation and division of the image, and creating sets each containing 644 sheets of images of 256×256 pixels. The actual amount of information becomes the amount of data of 256×256×3, because of containing color information as well. Prepared data sets were a set a in which a differentiated type and an undifferentiated type could be clearly distinguished from each other, and a set b in which an undifferentiated type component was mixed with a differentiated type component but the undifferentiated type component was absent/present (FIG. 6).

The deep learning to be used here is not particularly limited as long as the learning is a network suitable for image processing. Examples of a neural network having high image recognition capability include models of: Convolutional Neural Network (CNN); Vision Transformer (ViT), i.e., models used in field of natural language processing such as Transformer, Self-Attention or BERT (Bidirectional Encoder Representations from transformers) applied to an image system. Many of examples of convolutional neural networks have been developed in Image Recognition Competition (ILSVRC) using large-scale object recognition data sets (ImageNet), and the examples include ResNet, Inception-v3, VGG, AlexNet, U-Net, SegNet, Densenet and Squeezenet; and new models for image recognition such as EfficinentNet, Big Transfer (BiT), and ResNeSt can also be used. Furthermore, it is needless to say that a model with high image recognition capability can be used, which will be developed in the future.

Example 1

Figure 6:
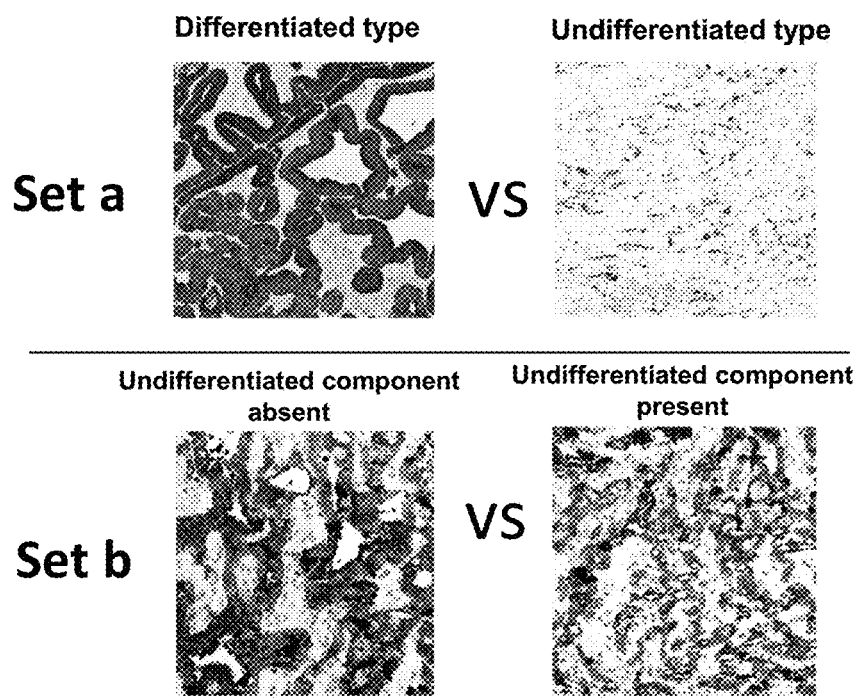
FIG. 6 shows diagrams showing an example of an image data set prepared for learning.

Firstly, transfer learning was performed in ResNet with the use of an immunohistochemically stained specimen based on cytokeratin, by using a data set of a differentiated type and an undifferentiated type which are easily determined as shown in Set a (FIG. 6). The transfer learning is used for a new task by using a pretrained network and a parameter value. The learning system was caused to learn through both of transfer learning that uses an initial value of parameters (weights) which ResNet learned through a large-scale data set, and is caused to learn by own image data, and Scratch learning which causes a model to learn own image data by using only a structure of the model without using the initial value of the learned parameter.

In the present invention, the following instrument systems were used.

Figure 7:
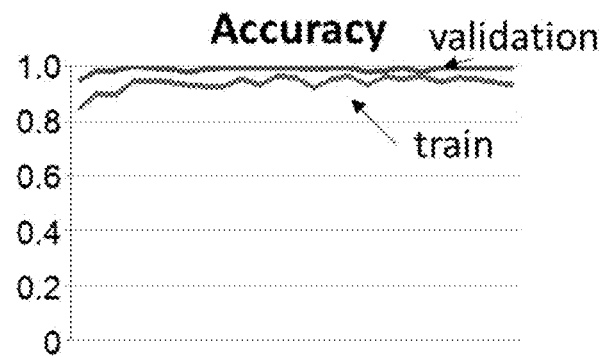
FIG. 7 shows diagrams showing scratch learning, training by fine tuning, and the accuracy of validation, which use the differentiated type/undifferentiated type image data set.
Figure 7:
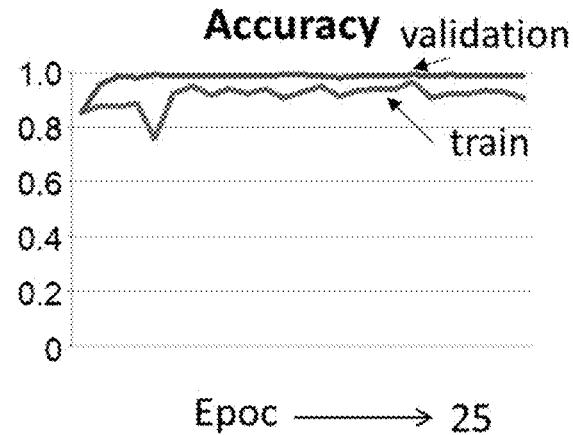

A; CPU; Intel corei7, and GPU None
B; CPU; Intel corei7, and GPU NVIDIA GeForce 1080-Ti
C; CPU; Intel Xeon, and GPU NVIDIA GeForce RTX 2080-Ti
D; CPU; Intel corei9, and GPU NVIDIA Titan-V In the training with the use of the data set a which was created from the immunohistochemically cytokeratin-stained specimen of differentiated/undifferentiated gastric cancer, the recognition accuracy was 0.9609 by Scratch learning, and 0.9883 by transfer learning (fine tuning); and sufficient recognition accuracy was obtained (FIG. 7).

Figure 8:
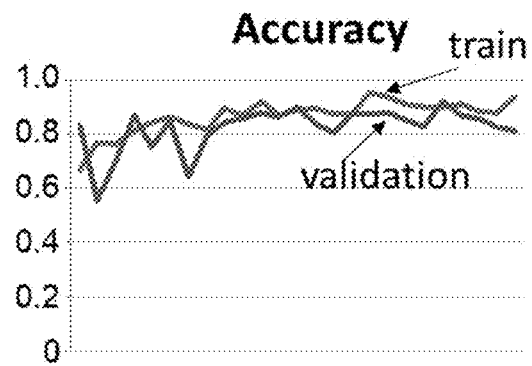
FIG. 8 shows diagrams showing scratch learning, training by fine tuning, and the accuracy of the validation, which use the image data sets in which differentiated and undifferentiated types are not mixed/are mixed.
Figure 8:
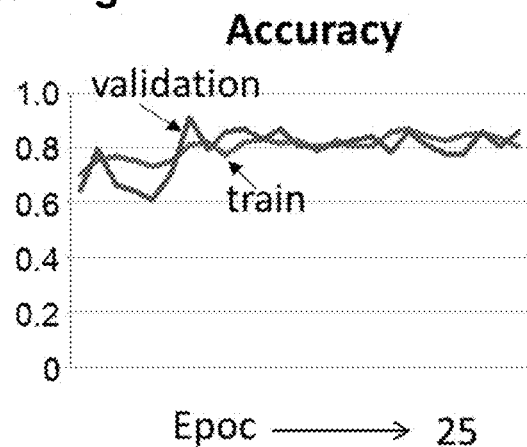

Next, in the training with the use of Set b (FIG. 6), which was an immunohistochemically cytokeratin-stained specimen of gastric cancer in which a mixture of the undifferentiated component is absent and present, the recognition accuracy was 0.9219 by the Scratch learning and 0.9102 by the transfer learning (fine tuning); and also, in the case of this data set, sufficient recognition accuracy for being used for diagnosis assistance was obtained (FIG. 8). The specimens in which the mixture of the undifferentiated component is absent and present are tissue images that are highly difficult even for a pathologist. In the case of the data set for which the decision is difficult even for a pathologist, a correct answer rate by AI becomes low, but even in the case, the correct answer rate of 90% or higher can be obtained, and accordingly, it is considered that there is sufficient accuracy.

Overfitting refers to a phenomenon in which a generalization performance decreases due to a phenomenon that parameters specific to training data result in being trained, and accuracy in validation data results in decreasing. In order to prevent overfitting, it is the best solution to increase training data, but there is data augmentation as a method of efficiently increasing the training data based on a small amount of data. The data augmentation is a method of increasing the training data by subjecting an image of the training data to processing such as rotation, deformation, extraction of a central portion, enlargement and shrinkage. Here, too, the image for training is subjected to data augmentation by these processes.

By the image data being subjected to the deep neural network, an essential feature (also referred to as latent representation or internal representation) of the input image is extracted, while the dimension of data is sequentially reduced. There is an autoencoder as one of methods for obtaining the feature (latent representation or internal representation) from data. This is a method of extracting the feature (latent representation or internal representation) from original data by an encoder, and restoring the original data based on the feature by a decoder. In the case of image data, a convolutional neural network can be used in a portion of an encoder, which can also be considered that the neural network is used as a method of extracting the latent representation. By a classifier created by transfer learning being used as a feature extractor, a feature is extracted from an image patch which is created for an image for diagnosis, and further by a dimension being reduced to two dimensions, a distribution diagram of the feature which has been obtained from a tissue morphology can be visualized as a scatter diagram. The dimension of the feature is further reduced to two dimensions from the image patches which have been created from the tissue specimens of differentiated and undifferentiated gastric cancers, the two-dimensional distribution of morphological feature can be visualized as a scatter diagram.

Figure 9:
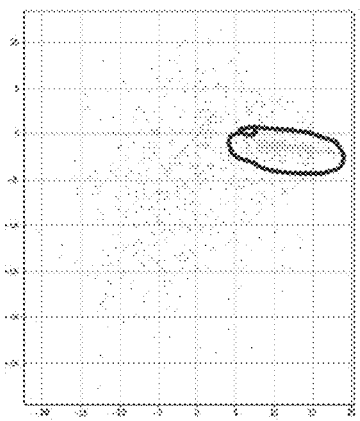
FIG. 9 shows a diagram schematically showing a state of visualizing a two-dimensional distribution of morphological feature from image patches of an image for diagnosis as a scatter diagram, and representing localization of image patches from which points of the scatter diagram are derived, in the whole lesion.
Figure 9:
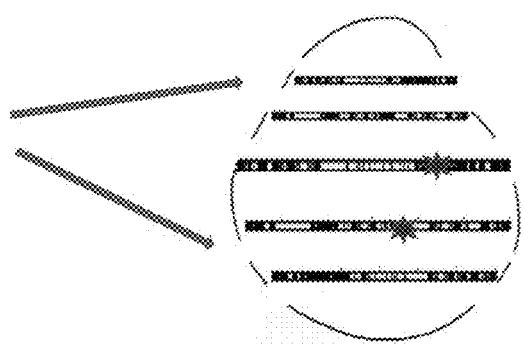

The left of FIG. 9 shows a two-dimensional scatter diagram of the morphological feature existing in the tumor, in which the dimension is already reduced. In the image patch which is created for the image for the diagnosis, a comprehensive image patch of the pathological tissue morphology contained in an individual tissue is obtained together with positional data in the tissue. For this reason, it becomes possible to cluster tumors having a marginal morphology which has been difficult to be determined by the conventional two division method based on differentiation and undifferentiation, with the use of the scatter diagram. Furthermore, it becomes also possible to know how the cluster of the feature is actually distributed in the tumor, by tracing the place in the lesion, in which the image patch exists from which the individual points of the scatter diagram are derived (right in FIG. 9).

The use of the feature and latent representation extracted from the histopathological image makes it possible that the feature is concatenated or fused with a feature obtained from data of different type of modality other than the image. Thereby, the feature can be used for multi-modal learning which infers the result, by combining feature of different modalities to each other. It becomes possible to use such a process that the information of the different modalities complementarily acts on the inference of the result, by combining the feature itself of the histopathological image with the feature extracted from the data of another modality of a different type, instead of the conventional classification categories such as the differentiated type and the undifferentiated type. For example, in clinical decision making such as decision on a therapeutic strategy, a system can be constructed which forms a decision by fusing data of different formats such as categorical data such as sex, numerical data such as examination data, image data such as a radiation image, and information on genetic alterations.

Example 2

[Creation of Reconstruction Map]

Figure 10:
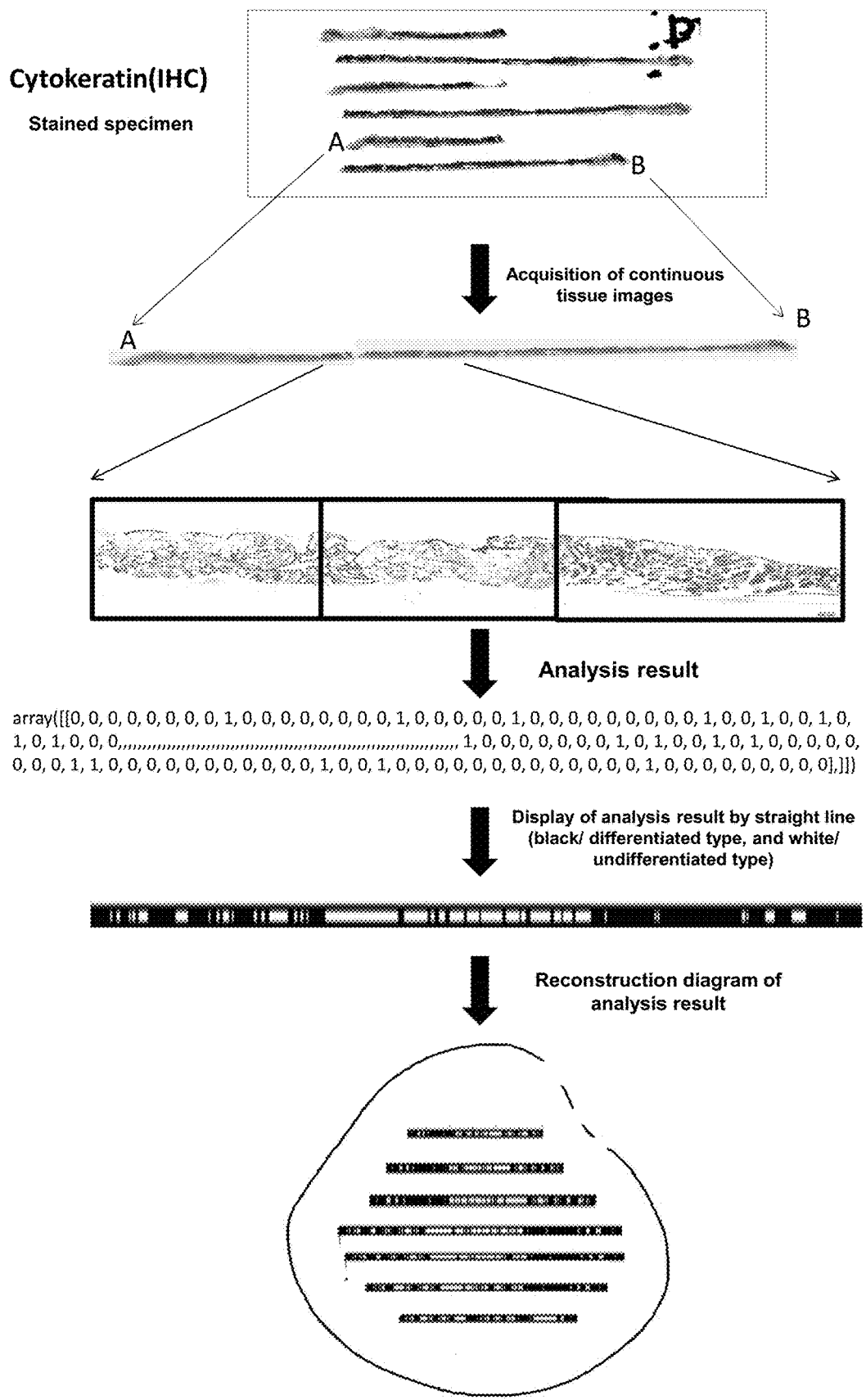
FIG. 10 shows diagrams showing a flow of pathological diagnosis assistance with the use of a pathological diagnosis assisting device.

With the use of the decision system constructed in the above, analysis and reconstruction were performed that used a tissue specimen of gastric cancer in which differentiated and undifferentiated components were mixed (FIG. 10). In this example, a model is constructed which has been caused to learn with the use of immunohistochemically stained specimens based on cytokeratin, and is used for determination.

A cut out tissue sections are arranged in parallel on a specimen prepared slide. In a case where the length of one slice of a tissue specimen is larger than a slide glass, the specimen is cut into two long and short pieces (A and B) so that the specimen fits on the slide glass as shown in FIG. 10, and the specimen is prepared. Histological images are continuously acquired from one piece of slice, which is synthesized from A and B on the cytokeratin-stained specimen, while a photographing field of view is moved. Here, three consecutive images are shown. Along with image acquisition, the coordinates are collected which are the coordinates of the starting point of each slice of the tissue specimen and the coordinates of the starting point of the cancer portion. The above consecutive images are subjected to a dividing process, and images each having 256×256 pixels are generated. In addition, in the classifier which used the immunohistochemically stained specimen based on cytokeratin, a high accuracy rate was obtained even when slightly different tissue components were included in the training image, and accordingly analysis by images at low magnification was possible. Because of this, in this example, the vertical direction (thickness direction of mucous membrane) could be covered with one row of image patches.

The divided images are numbered in the horizontal direction, and their order on the original specimen slice are retained. The above image set is analyzed with the previously created classification and decision systems. The analysis result, in which decision of a differentiated type or an undifferentiated type is set with 0 and 1, is output, and stored as a one-dimensional vector. The systems convert the one-dimensional vector obtained from one slice to two-dimensional vector, convert a value 1 of the vector into a value 255, and make the values of 0 and 255 correspond to two colors of black and white, respectively. The systems draw the obtained two-dimensional vector as an image, and obtain a straight line in which a differentiated type and an undifferentiated type are indicated by black and white. In this example, white corresponds to the undifferentiated type, and black corresponds to the differentiated type.

Here, the same one-dimensional vector is doubly nested and is thereby converted to two-dimensional vector with the use of NumPy, and then the two-dimensional vector is drawn as a straight line with the use of pyplot module of a graph drawing package Matplotlib that functions under NumPy. For information, the NumPy is a library that provides a manipulation of a multi-dimensional array and a numerical calculation function under a development environment in the Python language. Here, the one-dimensional vector of the analysis result output from the decision system is doubly nested, is converted into two-dimensional vector with the use of the NumPy, and the two-dimensional vector is drawn as a straight line with the use of the pyplot module.

The straight lines obtained from each slice are arranged on the basis of the coordinates of the start point of each slice and the coordinates of the start point of the cancer portion, and thereby a reconstruction diagram of the analysis result for the whole specimen can be obtained. As shown in this example, the use of deep learning, which has been previously used only to determine the existence of lesions, is further developed and reconstructed into a pattern that can comprehensively determine cancer lesions on the basis of information on the degree of differentiation and position of cancer lesions. As a result, it becomes possible to draw a map of the degree of undifferentiation of a cancer lesion, to decide the position and size of an undifferentiated component at a glance, and to quickly determine the risk of metastasis and the like.

In addition, there is a limit in precisely drawing the result of the degree of differentiation, which has been decided by a pathologist through observation under a microscope, on the section line of the whole specimen diagram, and particularly when cancer tissue having different degrees of differentiation are mixed in a very narrow area, it is difficult to precisely map and reproduce the distribution. Accordingly, there is a natural limit to the precision of the reconstruction diagram created by a human, and it also takes a lot of time to create the reconstruction diagram. By using the method developed this time, it is possible to create a precise map, which can greatly contribute to the selection of therapeutic methods.

When a pathologist observes an actual specimen using the present system, he/she corrects the reconstruction diagram by the AI based on his/her own observation result while referring to the reconstruction diagram created by the AI, and completes the reconstruction diagram for the diagnosis report. Thereby, not only the precision of the reconstruction diagram is remarkably improved, but also the time necessary for creating the diagnosis report can be greatly reduced.

Example 3

The pathological diagnosis assisting method by the HE-stained image will be described. The pathological diagnosis in actual clinical practice is performed mainly with the use of the HE-stained specimen. In order to further increase the versatility of a classifier constructed with an immunohistochemically stained specimen based on cytokeratin, a classifier using an HE-stained specimen is necessary. A data set for training composed of the HE-stained specimen was prepared, and firstly, a two-class classifier for differentiation type and undifferentiation type of gastric cancer was constructed (FIG. 11).

In order to create a classifier having a high accuracy rate, an image data set for training is important. A large number of image data sets for training were prepared which included two classes of the differentiated type and the undifferentiated type, as shown in FIG. 11(A). Histomorphological components contained in one sheet of image for training are controlled to be single as much as possible, and the image for training is prepared so as not to include a multiple of components. However, the size of the image itself is specified so as to be 224×224 pixels, 299×299 pixels or the like, by the convolutional neural network to be used in the classifier, and accordingly, the image is prepared so that a small region consisting of only single morphologic components fits in the size. Also in a case where a large image is divided and an image of a specified size is obtained, the size of the division is examined so that the divided image satisfies the above conditions.

Next, one model is adjusted so that the accuracy rate becomes high in the validation data, while changing learning conditions. FIG. 11 shows an example of a learning curve when Resnet 18 has been used as a model. In the study of a baseline, the variation in the accuracy rate in the data for validation (val) for each epoch is large (FIG. 11(B)). Then, the learning curve was improved from the baseline to 1 (FIG. 11(C)) and 2 (FIG. 11(D)), by adjustment of a learning rate and adjustment of a batch size. In the learning curve of 2, a tendency of overfitting was not generally observed, and an obtained highest value of the accuracy rate in the data for validation was 0.9683.

Example 4

Figure 12:
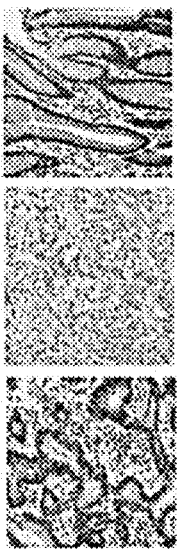
Figure 12:
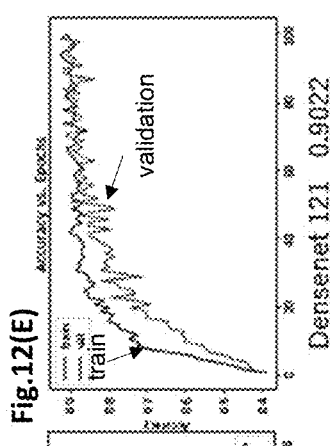
Figure 12:
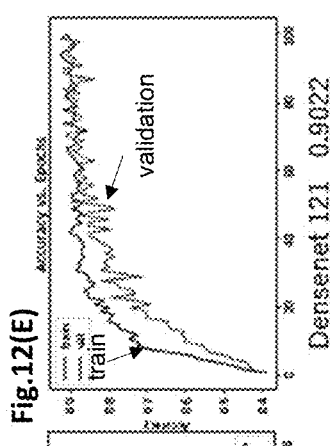
Figure 12:
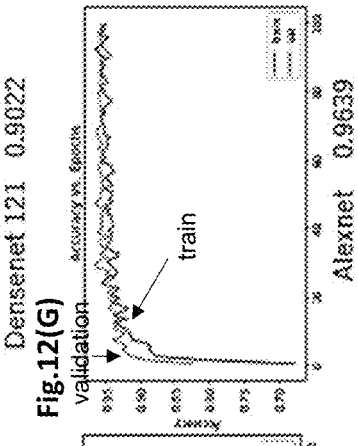
Figure 12:
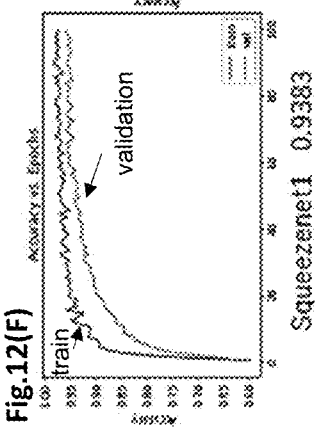
Figure 12:
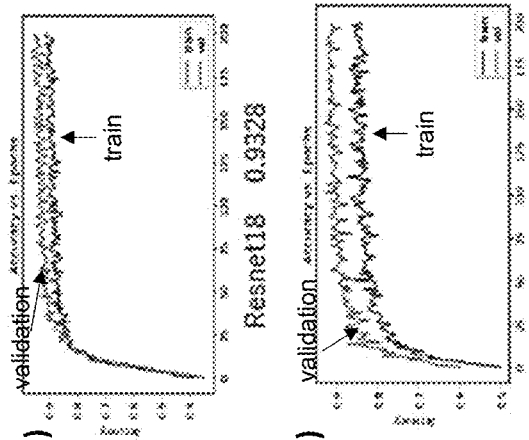

A classifier having a high accuracy rate was created with the use of a data set of three classes for training, in which a normal tissue was added to the differentiated type and undifferentiated type of gastric cancer, while six models were compared (FIG. 12). Typical tissue images of the differentiated type, the undifferentiated type and the normal tissue are shown in FIG. 12(A). A classifier was created with the use of these image data sets for training, and with the use of six models. There are a number of models that can be used for image classification by transfer learning, and any model is a model which has been evaluated in the image recognition competition using the ImageNet data set, or a modified version thereof. In Resnet 18 (FIG. 12(B)) and Inception V3 (FIG. 12(C)), the highest values of the accuracy rates of 0.93 and 0.92 or more were obtained in the data for validation, and in Alexnet (FIG. 12(G)), an accuracy rate of 0.9639 was obtained. In addition, in Densenet 121 (FIG. 12(E)), the generalization capability is barely starting to appear after learning of 100 epochs, and there is a possibility that sufficient generalization capability is obtained if the learning beyond 100 epochs will be performed. On the other hand, in Vgg 11_BN (FIG. 12(D)) after 60 epochs and in Squeezenet 1 (FIG. 12(F)), a tendency of overfitting is recognized. In this way, such a method can be applied to an actual clinical diagnosis as to acquire parameters in an optimal model and epoch in which the generalization performance can be obtained without falling into overfitting, while viewing the learning curve.

Example 5

Next, it will be shown that the pathological diagnosis assisting method shown in the Examples can be applied not only to gastric cancer but also to various cancers. In the present specification, a pathological diagnosis assisting method is described in which a training data set is prepared, a model suitable for the training data set is selected, and the transfer learning is performed; and the parameters are stored, and are used in a classification system. This series of processes can be used not only for the differentiation/undifferentiation type of gastric cancer, but also for cancers of other organs. In various cancers other than gastric cancer, it is known that there exists a mixture of histological types in the same tumor, and examples of tumors which have been described in the Classification of Cancer include endometrial cancer, thyroid cancer, and breast cancer. For example, in thyroid cancer, in a case where a well-differentiated component (papillary cancer or follicular cancer) and a poorly differentiated component are mixed, the case where 50% or more of the mixture is occupied by the poorly differentiated type is described as the poorly differentiated type. Endometrial cancer is classified into three stages according to the proportion of the types in a tumor. Also in such a case, if image data sets for training of the well-differentiated type and the poorly differentiated type are constructed respectively, and a classifier is created, it becomes possible to create a map of the well-differentiated type/poorly-differentiated type.

Figure 13:
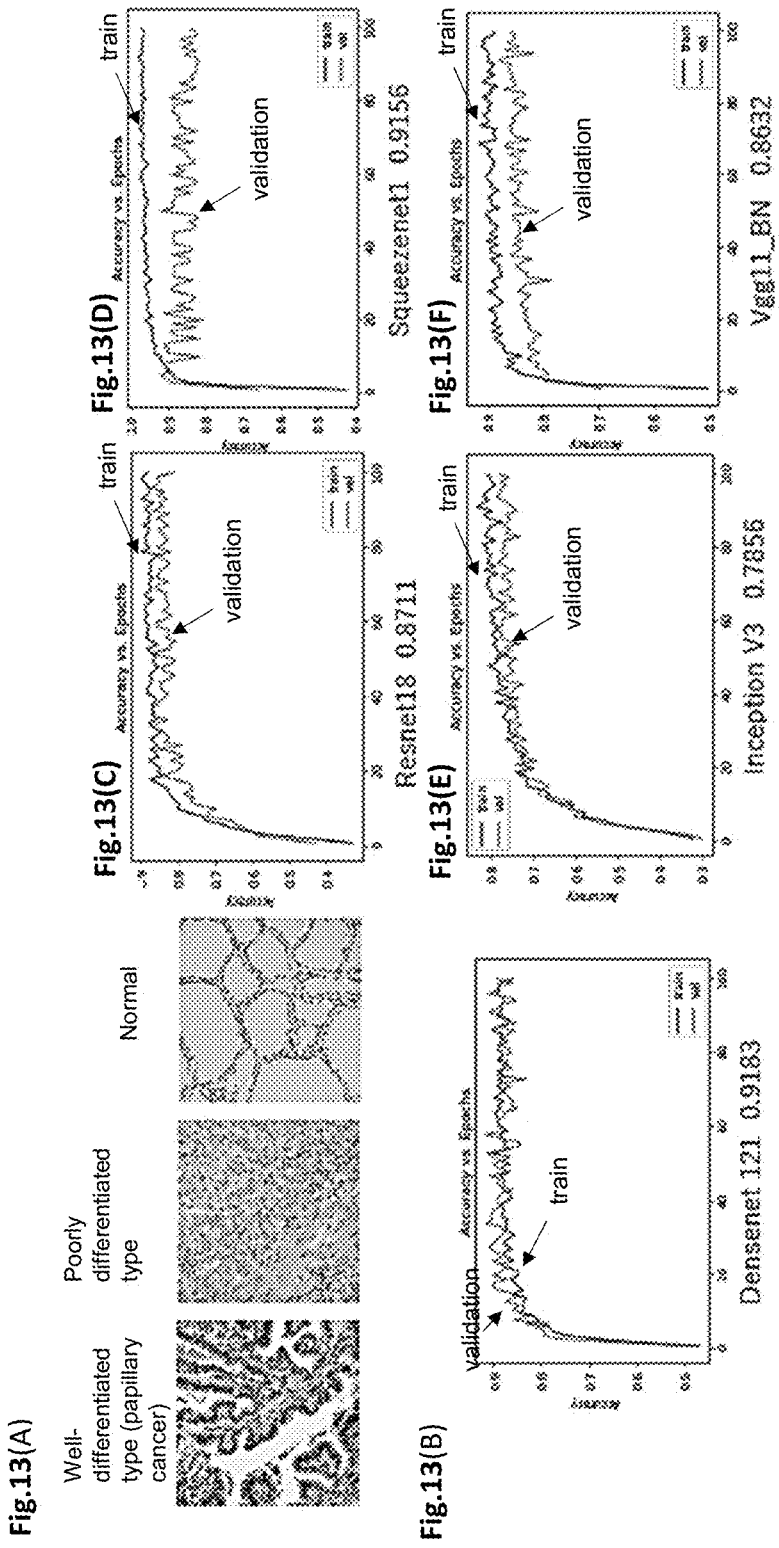

An example of construction of a training model in thyroid cancer is shown (FIG. 13). A model was constructed from classification of three classes (FIG. 13(A)) which were a well-differentiated type (papillary cancer) and a poorly differentiated type of thyroid cancer, and a normal thyroid gland tissue. In this data set of the thyroid gland, Resnet 18 (FIG. 13(C)), Inception V3 (FIG. 13(E)), Squeezenet 1 (FIG. 13(D)) and the like tend to easily fall into overfitting, but in Densenet 121 (FIG. 13(B)), it is possible to obtain a model having an accuracy rate of about 90% by stopping learning at about 40 epochs and obtaining parameters. In addition, in Vgg 11_BN (FIG. 13(F)), the accuracy rate in the validation data tends to increase slightly, and accordingly, it is considered that the accuracy rate is improved by further increasing the number of epochs and performing the learning. As shown in the examples of gastric cancer and thyroid cancer, the optimal model for each organ is different. Accordingly, it is necessary to select a model for each organ and select a model having a high accuracy rate.

Example 6

The pathological diagnosis assisting method can be used for tumors in which a pathognomonic pathological tissue image is known that is related to a change or expression of a gene, by preparing a training data set, selecting a model suitable for the training data set, storing the parameters, and using the parameters in a classification system. A vast amount of information has been accumulated on changes in genes and proteins associated with cancer; and among the changes, in the case of a change in which a relation to histomorphological information is known, a policy as to what biological searches for the gene or cell should be performed can be determined, by classifying on the basis of the histomorphological information. In addition, such classification is considered to assist also in recommending orders of further examinations.

In The Cancer Genome Atras (TCGA) by NCI (National Cancer Institute), it is known that gastric cancer is roughly divided into the following four molecular subtypes (Non Patent Literature 4).

Chromosomal Instability (CIN)
Genomically stable (GS)
Microsatellite instability (MSI)
Epstein-Barr Virus (EBV)

Among the subtypes, in MSI and EBV types of gastric cancers, a pathognomonic tissue image is known in which lymphocytes remarkably infiltrate into a tumor. In addition, in cancers contained in GS, a histologically diffuse type (poorly differentiated adenocarcinoma) occupies a majority, and among the types, several groups are known which involve changes in genes.

A method of estimating MSI from an HE-stained image with the use of deep learning has already been reported (Non Patent Literature 5). In the case of gastric cancers which are accompanied by overexpression/gene amplification of HER2 protein, medical treatment with molecularly targeted drugs has been carried out, and companion diagnosis by immunohistochemical and FISH methods has been established. Accordingly, if the overexpression/gene amplification of the HER2 protein in addition to MSI can be estimated by the HE staining, HER2 positive gastric cancer is not missed in the stage of the pathological diagnosis by the HE staining, and more appropriate treatment can be performed. In such HER2 positive gastric cancer, it is known that the frequency of the overexpression of the HER2 protein is significantly higher in an intestinal type (tubular adenocarcinoma) between the intestinal type (tubular adenocarcinoma) and a diffuse type (poorly differentiated adenocarcinoma and the like) according to Lauren classification, and in a case where the intestinal type (tubular adenocarcinoma) and diffuse type of tissue images are mixed, companion diagnosis in a specimen containing a lot of the intestinal type is recommended.

Figure 14:
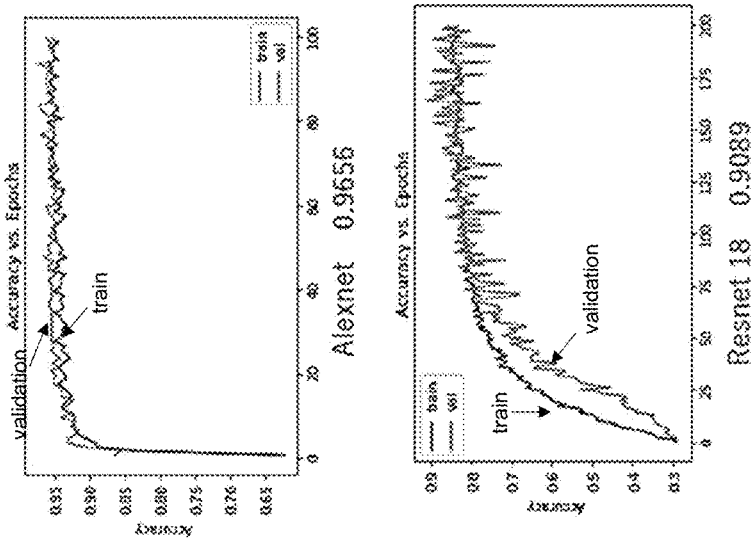
FIG. 14 shows diagrams showing the construction of a classifier with the use of pathognomonic pathological tissue images associated with changes and expression of genes, and the results.
Figure 14:
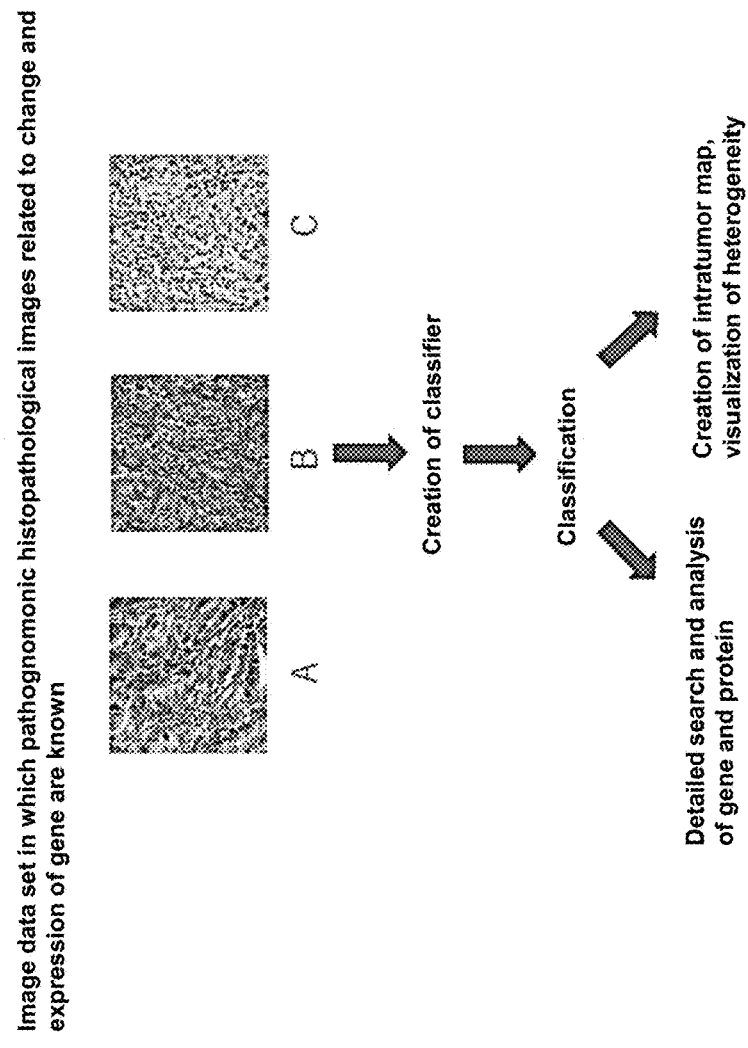

FIG. 14 shows results of preparing a training image data set with the use of a tissue image (A) obtained from a cancer tissue having the overexpression/gene amplification of the HER2 protein, a tissue image (B) obtained from a cancer tissue in which MSI was confirmed, and a tissue image (C) obtained from a cancer tissue in which a mutation occurs in a gene found in a diffuse type cancer, and classifying three classes. Images classified into three classes were trained, a classifier was created, and the classifier was validated with images for diagnosis. In Alexnet, an accuracy rate of 0.9656 was obtained, and in Resnet 18, an epoch twice that of Alexnet was required for training, but an accuracy rate of 0.9089 was obtained.

When a pathognomonic pathological tissue image is known which is associated with a mutation or expression of a gene, a change in the mutation or expression of the gene can be estimated from the pathological image. As shown in the Examples, if the possibility of the overexpression/gene amplification of the HER2 protein can be indicated at the time of the pathological diagnosis by the HE staining, a definitive diagnosis can be made by immunohistochemistry staining and the medical treatment which targets the HER2 can be performed. A pathologist in a facility having a large number of cases (high volume center) grasps rough features of such pathological tissue images related to the mutation or expression of a gene, in many cases. It becomes possible to implement such accumulation based on the experience of experts, in a pathological diagnosis assisting system as a classifier. Furthermore, if the accuracy of the diagnosis becomes high, it becomes also possible to select molecular-targeted drugs using the HE staining as a companion diagnosis. In the Example, the training image data set of the above three classes is prepared and classified, but if a change of a gene or a pathognomonic tissue image associated with the change is newly known, a new class can be sequentially added, and a classifier can be sequentially created.

Example 7

When a differentiated/undifferentiated map is actually created from an endoscopic resection specimen using a classifier created from an image data set of the HE-stained specimen, three to five image patches are obtained in the vertical direction according to the thickness of the mucous membrane. FIG. 15(A) shows an example in which three image patches are obtained in the vertical direction. This example shows image patches of the gastric mucosal lamina propria in the HE specimen, which consist of three sheets in the vertical direction and ten sheets in the horizontal direction.

In the middle row of FIG. 15(B), in this image patch, the patches are shown by a gray color, which are determined to be normal in the classification result, the differentiated type is shown by black, and the undifferentiated type is shown by white. In the lower row, a map is shown in which a part in which even one of three image patches in the vertical direction is determined to be undifferentiated is determined to be undifferentiated, for each vertical column. Here, in the case where there is at least one patch which is determined to be undifferentiated, in each vertical column, in other words, in the thickness direction, a criterion which determines the case to be undifferentiated is provided; but it is possible to freely change the criterion that in what case a horizontal map in which a column is determined to be undifferentiated should be created, in the case where several patches among patches in the thickness direction are determined to be undifferentiated. Due to such processing being performed, it becomes possible to perform decision even in the case where a lesion is elevated or in the case where a small image patch is used.

Example 8

Figure 16:
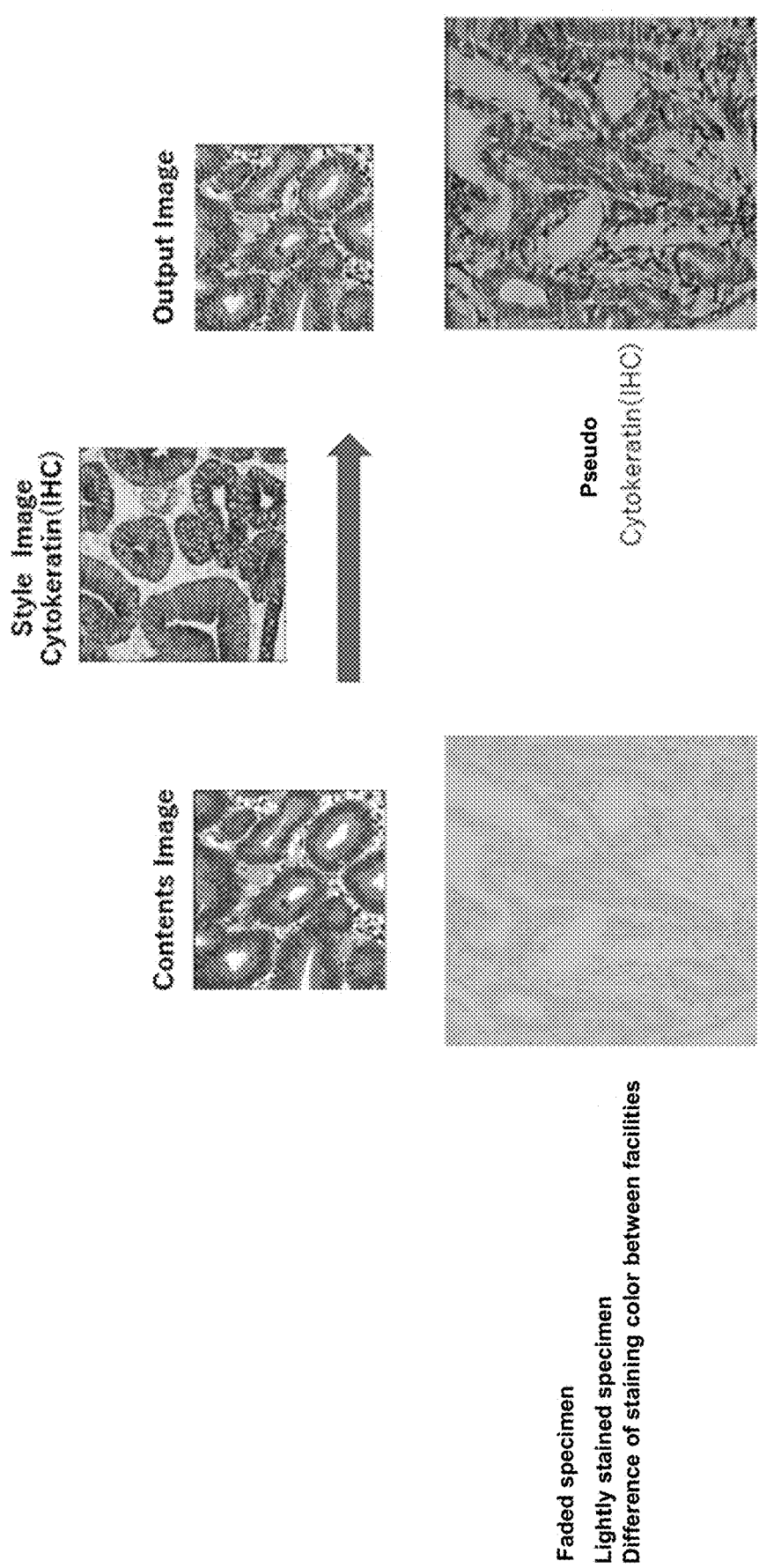
FIG. 16 shows a diagram showing processing of an image with the use of neural style transfer.
Figure 17:
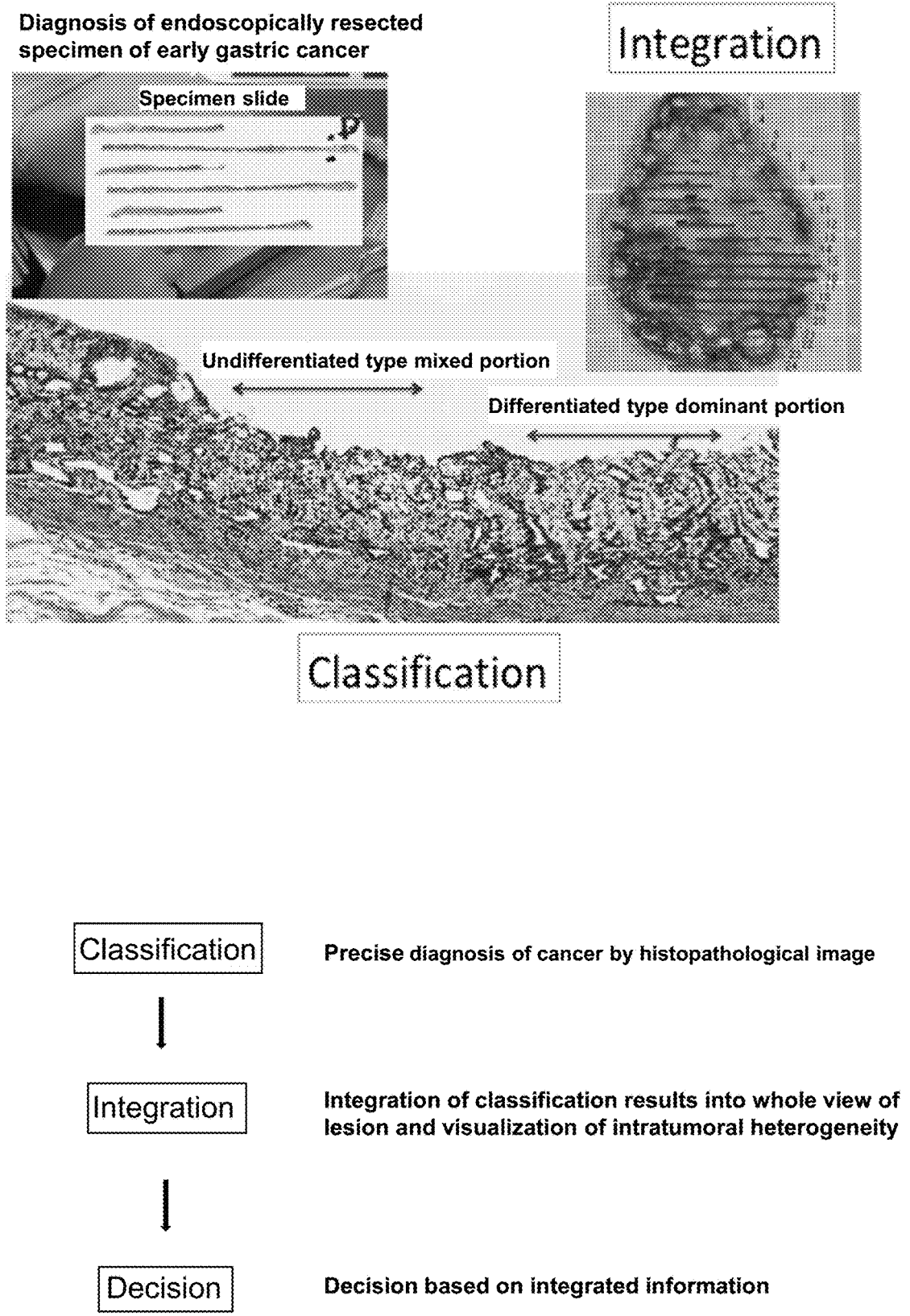
FIG. 17 shows a diagram showing a flow of a pathological diagnosis according to the prior art.

In a pathological diagnosis in an actual clinical practice, the HE-stained specimen is mainly used; but there is a specimen in which fading has progressed with time, a specimen in which stained color is light, and specimens of which the colors are different between facilities. As a countermeasure against such specimens, a neural style transfer (Non Patent Literature 6) can be utilized, which uses a convolutional neural network. This neural style transfer is a method of processing the specimen with the use of a technique such as a Neural-Style algorithm, which regards a feature, a color and a texture independent of a position in the image, as a style image, with respect to a content image corresponding to a global picture composition of an image. An example is shown (FIG. 16), in which an image of a specimen in which the fading has progressed is converted into that of an immunohistochemically stained specimen based on cytokeratin, by Neural style transfer. An image which has been converted to pseudo-cytokeratin (IHC)-stained image can be determined by a classifier which has been constructed with cytokeratin-stained specimens, and a map can be created.

In the present specification, it has been shown that the present diagnosis assisting method can be applied to gastric cancer and thyroid cancer with the use of the HE-stained specimens; but if an appropriate model is selected, the diagnosis assisting method using the model can determine the histological type of cancer in any organs, can visualize and provide a bird's-eye view of heterogeneity in tumors, and thereby can be used for the pathological diagnosis assistance. In addition, an example has been shown in which the histological type is determined based on an image by immunohistochemistry staining based on cytokeratin in gastric cancer, but if an image of immunohistochemistry staining is used which is not only based on cytokeratin but also based on a protein serving as an index of malignancy of cancer or a protein indicating reactivity to medical treatment (biomarker), the diagnosis assisting method can create a malignancy map or a treatment reactivity map of a tumor, and provide the bird's-eye view of the heterogeneity in the tumor. In addition, as shown in Examples, the fact that a cancer in which the overexpression of HER2 is suspected can be decided from the HE image indicates that the method can be applied to digital companion diagnosis.

The morphology on which the pathological diagnosis is based, specifically, histological findings of typical normal tissues, benign tumors, malignant tumors (cancer and sarcomas) and the like are described in books of histology and pathological diagnosis, and are shared. Furthermore, the histological findings are inherited in the course of training until regular doctors become pathological specialists, and are clearly defined in Japanese Classification of Cancer and WHO classification, and are shared in places such as academic conferences and case study conferences. However, difference in tissue morphology is continuous, and there are not a few cases in which diagnosis is difficult in actual clinical practice, such as the difference between a normal tissue and a tumor, and the difference between the differentiated type and the undifferentiated type in a tumor; and subtle decisions are ultimately left to individual pathologists. It is also well known that in the case of gastric cancer, the determination of intramucosal carcinoma differs between Japan and the West. Also in the case of histological findings for which the consensus is not consistent, according to this method, it is also possible to easily examine the relationship between the result of the present system and the prognosis, again, on the basis of the past data, and examine the prognosis by confirming the past pathological data and the recurrence rate such as the lymph node metastasis rate. As a result, it is possible to provide an appropriate therapeutic method to patients based on the relationship between the selection of the therapeutic method and the prognosis, and contribute to the establishment of therapeutic methods for cancer in which the inside of the tumor is heterogeneous and for which it has been difficult to be determined until now.

The invention claimed is:

1. A pathological diagnosis assisting method including:
   an image acquisition step of continuously acquiring microscopical observation image data of a tissue specimen;
   a step of dividing the image data into a predetermined size while maintaining positional information on a whole specimen and positional information on a tissue image, and obtaining image patches;
   a determination step of determining a class for each image patch, according to a feature extracted by machine learning from data for training; and
   a reconstructing step of displaying determined classes at each position of the tissue images, and reconstructing the classes in the whole specimen.

2. The pathological diagnosis assisting method according to claim 1,
   wherein the reconstructing step of displaying the classes determined by machine learning at each position and reconstructing the classes in the whole specimen causes heterogeneity of a tumor to be displayed.

3. The pathological diagnosis assisting method according to claim 1,
   wherein the machine learning is based on a neural network.

4. The pathological diagnosis assisting method according to claim 3,
   wherein the neural network uses images having resolutions of 0.1 µm/pixel to 4 µm/pixel, as images for training.

5. The pathological diagnosis assisting method according to claim 1,
   wherein the tissue specimen is derived from a cancer tissue and pathological diagnosis of cancer is assisted.

6. The pathological diagnosis assisting method according to claim 1,
   wherein the tissue specimen is an HE-stained specimen or an immunohistochemically stained specimen.

7. The pathological diagnosis assisting method according to claim 6,
   wherein when the HE-stained specimen is a non-standardized specimen, a neural style transfer method is used, a quasi-immunohistochemically stained specimen is prepared, and the class is determined by a learned model that has learned an immunohistochemical stained specimen image.

8. A pathological diagnosis assisting system including:
   image acquisition means for continuously acquiring microscopical observation image data of a tissue specimen;
   image processing means for dividing the image data into image patches having predetermined sizes while retaining positional information on a whole specimen and positional information on a tissue image;
   classification means for determining a class for each divided image patch, according to a feature extracted by machine learning from data for training; and
   reconstructing means for displaying the classified class at each position, and reconstructing the classes in the whole specimen.

9. The pathological diagnosis assisting system according to claim 8,
wherein the image processing means comprises means for standardizing a histologically stained specimen.

10. The pathological diagnosis assisting system according to claim 8,
wherein the machine learning is a neural network.

11. The pathological diagnosis assisting system according to claim 10,
wherein the neural network uses a parameter value that has been obtained in advance by transfer learning.

12. The pathological diagnosis assisting system according to claim 8,
wherein a disease pathological diagnosis of which is assisted is cancer.

13. A pathological diagnosis assisting program causing a computer to execute processes of:

dividing acquired image data into a predetermined size while maintaining retaining positional information on a whole specimen and positional information on a tissue image;

using a trained model that has trained by use of data for training;

determining a class for each divided image patch, according to a feature extracted by machine learning from the data for training; and displaying the determined class at each position of the tissue image, and reconstructing the classes in the whole specimen.

14. The pathological diagnosis assisting program according to claim 13,
further comprising a process of continuously acquiring microscopical observation images of the tissue specimen.

\* \* \* \* \*